(12) United States Patent
Kitagawa et al.

(10) Patent No.: US 8,755,858 B2
(45) Date of Patent: Jun. 17, 2014

(54) BLOOD SENSOR, BLOOD TESTING DEVICE AND BLOOD ANALYSIS METHOD

(75) Inventors: Masahiro Kitagawa, Ehime (JP); Masaki Fujiwara, Ehime (JP); Keisuke Matsumura, Ehime (JP)

(73) Assignee: Panasonic Corporation, Osaka (JP)

( * ) Notice: Subject to any disclaimer, the term of this patent is extended or adjusted under 35 U.S.C. 154(b) by 454 days.

(21) Appl. No.: 12/866,308

(22) PCT Filed: Feb. 6, 2009

(86) PCT No.: PCT/JP2009/000488
§ 371 (c)(1),
(2), (4) Date: Aug. 5, 2010

(87) PCT Pub. No.: WO2009/098902
PCT Pub. Date: Aug. 13, 2009

(65) Prior Publication Data
US 2010/0324395 A1  Dec. 23, 2010

(30) Foreign Application Priority Data
Feb. 7, 2008  (JP) ................................. 2008-027462

(51) Int. Cl.
*A61B 5/05* (2006.01)

(52) U.S. Cl.
USPC ........................................................ 600/345

(58) Field of Classification Search
None
See application file for complete search history.

(56) References Cited

U.S. PATENT DOCUMENTS

| | | | |
|---|---|---|---|
| 6,733,493 B2* | 5/2004 | Gruzdev et al. | 606/9 |
| 2004/0220495 A1* | 11/2004 | Cahir et al. | 600/562 |
| 2005/0011759 A1* | 1/2005 | Moerman et al. | 204/403.03 |
| 2005/0123443 A1* | 6/2005 | Fujiwara et al. | 422/58 |
| 2005/0145491 A1* | 7/2005 | Amano et al. | 204/403.02 |
| 2006/0129065 A1* | 6/2006 | Matsumoto et al. | 600/583 |
| 2009/0043227 A1 | 2/2009 | Fujiwara et al. | |
| 2009/0177117 A1* | 7/2009 | Amano et al. | 600/583 |
| 2009/0318790 A1* | 12/2009 | Fujiwara et al. | 600/347 |
| 2009/0318834 A1* | 12/2009 | Fujiwara et al. | 600/583 |
| 2010/0042016 A1 | 2/2010 | Akiyama | |
| 2011/0137207 A1* | 6/2011 | Nishiuchi | 600/583 |

FOREIGN PATENT DOCUMENTS

| | | |
|---|---|---|
| EP | 1997432 | 12/2008 |
| JP | 2004-004046 | 1/2004 |
| WO | 2004/054445 | 7/2004 |
| WO | 2007/108515 | 9/2007 |

* cited by examiner

*Primary Examiner* — Michael Kahelin
*Assistant Examiner* — Mitchell Alter
(74) *Attorney, Agent, or Firm* — Greenblum & Bernstein, P.L.C.

(57) ABSTRACT

Provided are a blood sensor that is highly reliable and does not contaminate the interior of the main body of the device, a blood testing device and a blood analysis method. The blood sensor is provided with a plate-shaped base, a blood storage part set roughly in the center of the base, a supply path, one end of which is connected to the storage part and the other end of which is connected to an air pore, multiple detecting electrodes laid on one surface of the supply path connecting electrodes, each coming out of these detection electrodes, and skin detection electrodes in the storage part or near the storage part. The blood detecting device is provided with a skin detecting circuit that detects skin contact by measuring sensor conduction or impedance changes.

18 Claims, 25 Drawing Sheets

| VOLTAGE[V] | CURRENT AT NONCONTACT OF SKIN[$\mu$A] | CURRENT AT CONTACT OF SKIN[$\mu$A] |
|---|---|---|
| 1.00 | 0.0 | 32 |
| 2.00 | 0.0 | 70 |

FIG.24

| AT NONCONTACT OF SKIN C[pF] | AT NONCONTACT OF SKIN R[kΩ] | AT CONTACT OF SKIN C[pF] | AT CONTACT OF SKIN R[kΩ] |
|---|---|---|---|
| 1.79 | 88 | 3.25 | 2.0 |
| 1.79 | 86 | 3.76 | 2.7 |
| 1.79 | 86 | 3.07 | 6.0 |
| 1.79 | 86 | 3.20 | 10 |
| 1.79 | 81 | 2.80 | 6.3 |
| 1.80 | 75 | 4.3 | 2.2 |

FIG.26

BLOOD SENSOR, BLOOD TESTING DEVICE AND BLOOD ANALYSIS METHOD

TECHNICAL FIELD

The present invention relates to a blood sensor, a blood test apparatus and a blood analysis method to test blood by puncturing skin and so forth. The present invention relates to a blood sensor, a blood test apparatus and a blood analysis method to measure, for example, blood sugar levels, lactic acid levels or cholesterol levels.

BACKGROUND ART

The blood test apparatuses disclosed in Patent Document 1 and Patent Document 2 have been known as conventional blood test apparatuses.

FIG. 1 is a cross sectional view of a conventional blood sensor, and FIG. 2 is a plan view of a substrate constituting this blood sensor.

As shown in FIG. 1, blood sensor (or "sensor") 1 has a plate-like base body 2.

Blood storing section 3 is formed in approximately the center of base body 2. In addition, supply path 5 that supplies blood in storing section 3 to air hole 4 is provided in base body 2. One side of supply path 5 is coupled to storing section 3 and the other side is coupled to air hole 4. In addition, base body 2 is provided with detection electrodes 6 to 9 provided on the lower surface side of supply path 5 and connection electrodes 6a to 9a drawn, respectively, from these detection electrodes 6 to 9.

Base body 2 is composed of substrate 10 having an upper surface on which detection electrodes 6 to 9 and connection electrodes 6a to 9a are provided, spacer 11 that is provided on the upper surface side of substrate 10 and has a slit constituting part of supply path 5 and cover 12 provided on the upper surface side of spacer 11.

As shown in FIG. 2, wires in substrate 10 are respectively drawn to connection electrodes 6a to 9a formed in the end part 10a side of substrate 10 through detection electrodes 6 to 9 provided in substrate 10.

FIG. 3 is a cross sectional view of the blood test apparatus in which the above-described sensor 1 is mounted.

As shown in FIG. 3, blood test apparatus 17 has housing 18 having an approximately rectangular solid shape. Puncturing section 19 composed of upper holder 19a and lower holder 19b is provided in one corner of housing 18. Laser puncturing unit 20 is incorporated to face puncturing section 19.

Sensor cartridge 21 is removably inserted beside laser puncturing unit 20, and sensors 1 are stacked and stored in sensor cartridge 21. In addition, electrical circuit section 22 that measures the properties of blood 16 is arranged in parallel with sensor cartridge 21. Battery 23 is removably accommodated above laser puncturing unit 20, sensor cartridge 21 and electrical circuit section 22.

Puncturing button 20a to drive laser puncturing unit 20 is provided on upper surface 18b of housing 18, and skin detecting sensor 24 is provided in the vicinity of puncturing section 19 in the lower part of housing 18. In addition, a display section (not shown) is connected to electrical circuit section 22.

Now, operations of blood test apparatus 17 configured as described above will be explained.

First, slide plate 21a provided below sensor cartridge 21 conveys the bottom sensor 1 among sensors 1 stacked and stored, to puncturing section 19. Conveyed sensor 1 is sandwiched and fixed between upper holder 19a and lower holder 19b.

Next, the patient contacts puncturing section 19 with skin 15. This contact with skin 15 is detected by skin detecting sensor 24 provided in the vicinity of puncturing section 19 in housing 18. Puncturing is permitted by detecting the contact with skin 15. The patient then presses puncturing button 20a. When puncturing button 20a is pressed, laser light 20b is emitted from laser puncturing unit 20 and punctures skin 15.

Blood 16 exudes from skin 15 by puncturing skin 15. Exuding blood 16 is taken into sensor 1. Blood 16 taken into sensor 1 flows from storing section 3 into supply path 5 and is detected by detection electrodes 6 to 9. Signals detected in detection electrodes 6 to 9 are guided respectively to connection electrodes 6a to 9a and transmitted to electrical circuit section 22 through connection electrodes 6a to 9a. Electrical circuit section 22 measures components (e.g. a blood sugar level) of blood 16. Electrical circuit section 22 displays measurement results on a display section (not shown).

The puncturing apparatus described in Patent Document 2 has a detecting switch that detects swelling of skin in the apparatus and detects appropriate contact with skin by the detecting switch. The detecting switch is provided in a cylindrical part and has a movable body and a bracket each having a switch terminal. The movable body is pivotally supported by the shaft of the bracket and configured to change the position of the switch terminal. This movable body has a downward taper surface. When skin swells in the cylindrical part, the detecting switch rotates so as to allow the movable section to be lifted up by skin. By this means, the switch terminal of the movable body is shifted upward, and therefore, contacts the switch terminal of the bracket. As a result of this, the detecting switch is turned on and detects the contact with skin.

Patent Document 1: Japanese Patent Application Laid-Open No. 2004-4046
Patent Document 2: International Publication No. WO 2004/054445 Pamphlet

DISCLOSURE OF INVENTION

Problems to be Solved by the Invention

However, these conventional blood test apparatuses have a disadvantage that the detecting section that detects contact with skin is provided in the apparatus body, so that the detecting section is apart from the puncturing position. Therefore, it is not possible to assure of reliable contact with skin with the detecting section.

For example, in blood test apparatus 17 shown in FIG. 3, skin detecting section 24 is mounted in a site a little apart from storing section 3 in sensor 1, that is, mounted in the vicinity of puncturing section 19 in housing 18. Therefore, even if skin detection sensor 24 detects skin 15, it is not guaranteed that skin 15 completely contacts storing section 3. If skin 15 is punctured without contacting storing section 3, exuding blood 16 is not allowed to flow into storing section 3, so that blood test apparatus 17 is not able to accurately measure the properties of blood 16.

In addition, there is a problem that as a blood test apparatus is repeatedly used, the detecting section inside the apparatus body is stained. If the detecting section is left stained, the reliability of detection is decreased and also detection is performed under unsanitary condition, so that there is a risk of infection. Therefore, regular maintenance is required. However, maintenance of the inside of an apparatus body is troublesome and costly.

It is therefore an object of the present invention to provide a blood sensor, a blood test apparatus and a blood analysis method that are reliable and prevent the interior of the apparatus body from being stained.

Means for Solving the Problem

The blood sensor according to the present invention is a blood sensor that analyzes a component in a blood sample and adopts a configuration to include: a skin detecting section that is arranged to contact skin from which the blood sample is exuded; and a connection electrode that outputs a detection result by the skin detecting section to outside.

The blood test apparatus according to the present invention is a blood test apparatus in which the above-described blood sensor is mounted and that adopts a configuration to include a skin detecting circuit that detects contact or approach to skin based on a signal from the connection electrode.

The blood test apparatus according to the present invention adopts a configuration to include: the above-described blood sensor; an electrical circuit section connected to the blood sensor; and a battery that supplies power to the blood sensor and the electrical circuit section.

The blood test analysis method according to the present invention includes the steps of: a mounting step of mounting a blood sensor that is arranged to contact skin from which a blood sample is exuded and has a skin detecting section that detects contact with the skin, in an apparatus body; a detecting step of detecting contact or approach to the skin by receiving a detection result by a skin detecting section through a connection electrode; and an analyzing step of, when detecting contact with the skin, analyzing a component in the blood sample.

Advantageous Effects of Invention

According to the present invention, a sensor is provided with a skin detecting section that detects skin in a storing section or in the vicinity of the storing section, so that it is possible to check that skin reliably contacts the inside of storing section or the vicinity of the storing section. Since it is possible to certainly contact skin with the inside of the storing section and so forth, it is possible to make blood exuding from skin entirely flow into the storing section without flowing outside, so that it is possible to make good use of exuding blood. This allows accurate measurement of blood in the blood test apparatus side.

In addition, skin detecting section is provided in the blood sensor side, and sensors are disposable. Therefore, by using a new sensor each time, it is possible to prevent the interior of the apparatus body from being stained, so that sanitation is provided, and it is possible to prevent a risk of infection. In addition, maintenance is not necessary, so that it is possible to reduce the trouble and cost. A new sensor is provided every time the apparatus is used, so that deterioration in the accuracy of detection due to stains and so forth is prevented.

BRIEF DESCRIPTION OF DRAWINGS

FIG. 24 is a drawing showing a table of the result of an experiment using the blood test apparatus according to Embodiment 6;

FIG. 26 is a drawing showing a table of the result of an experiment using the blood test apparatus according to Embodiment 6.

BEST MODE FOR CARRYING OUT THE INVENTION

Now, embodiments of the present invention will be described in detail with reference to the accompanying drawings.

Embodiment 1

Figure 1:
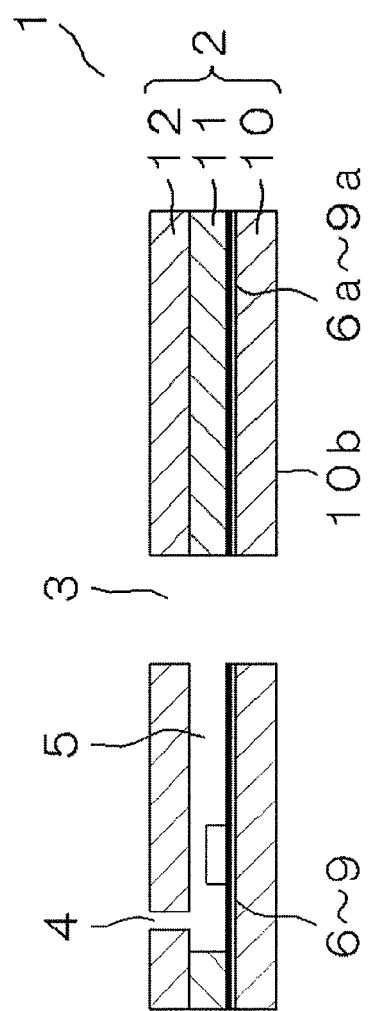
FIG. 1 is a cross sectional view of a conventional sensor.
Figure 2:
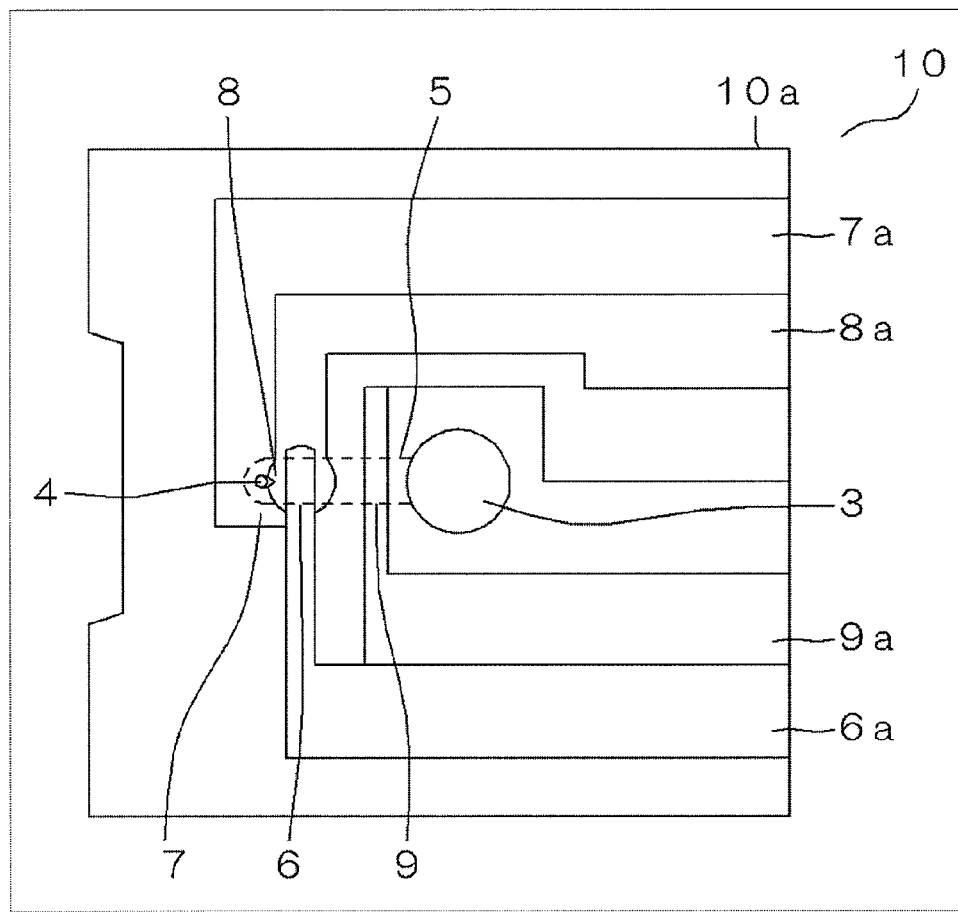
FIG. 2 is a plan view of a substrate constituting the conventional sensor.
Figure 3:
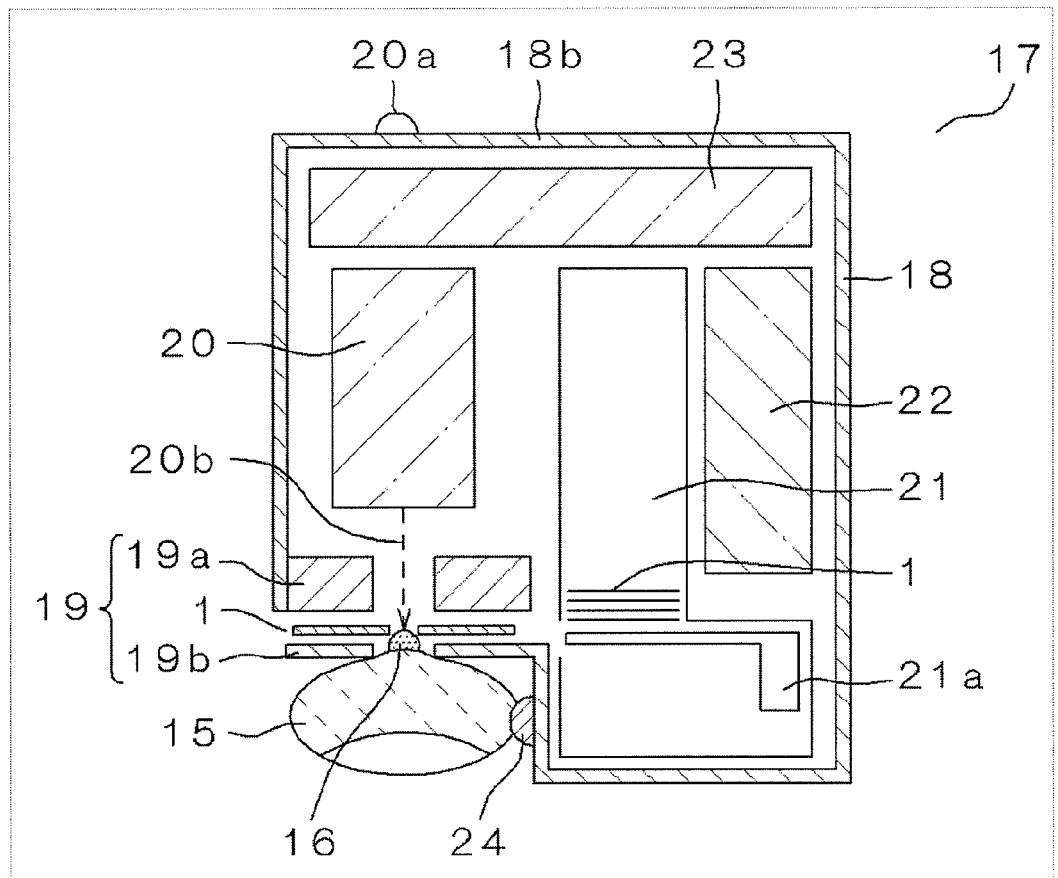
FIG. 3 is a cross sectional view of a blood test apparatus in which the conventional sensor is mounted.
Figure 4:
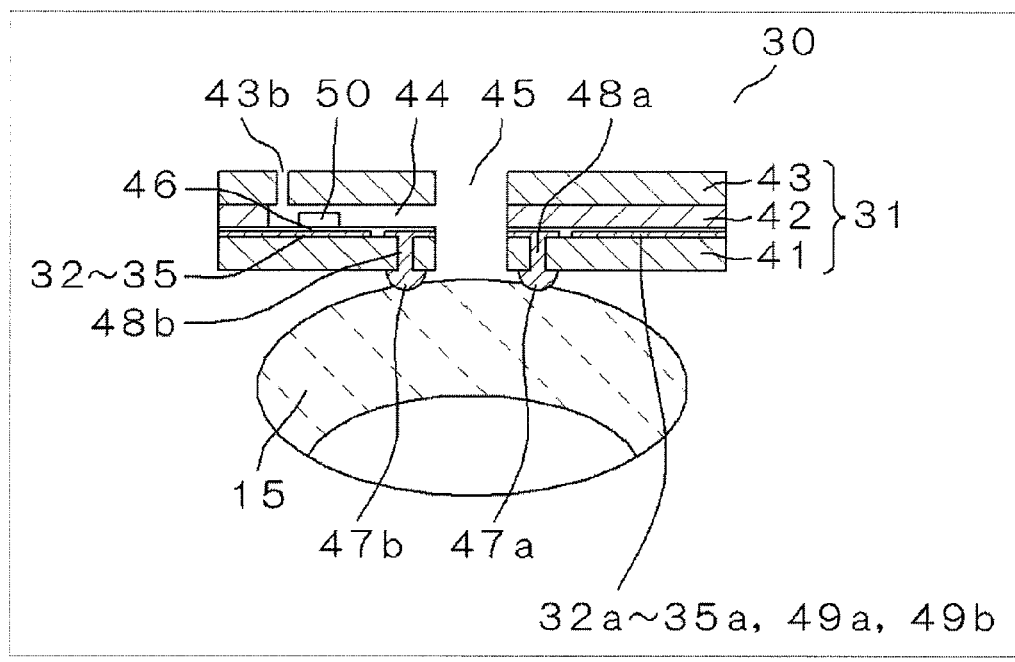
FIG. 4 is a cross sectional view of a sensor and its neighborhood according to Embodiment 1 of the present invention.
Figure 5:
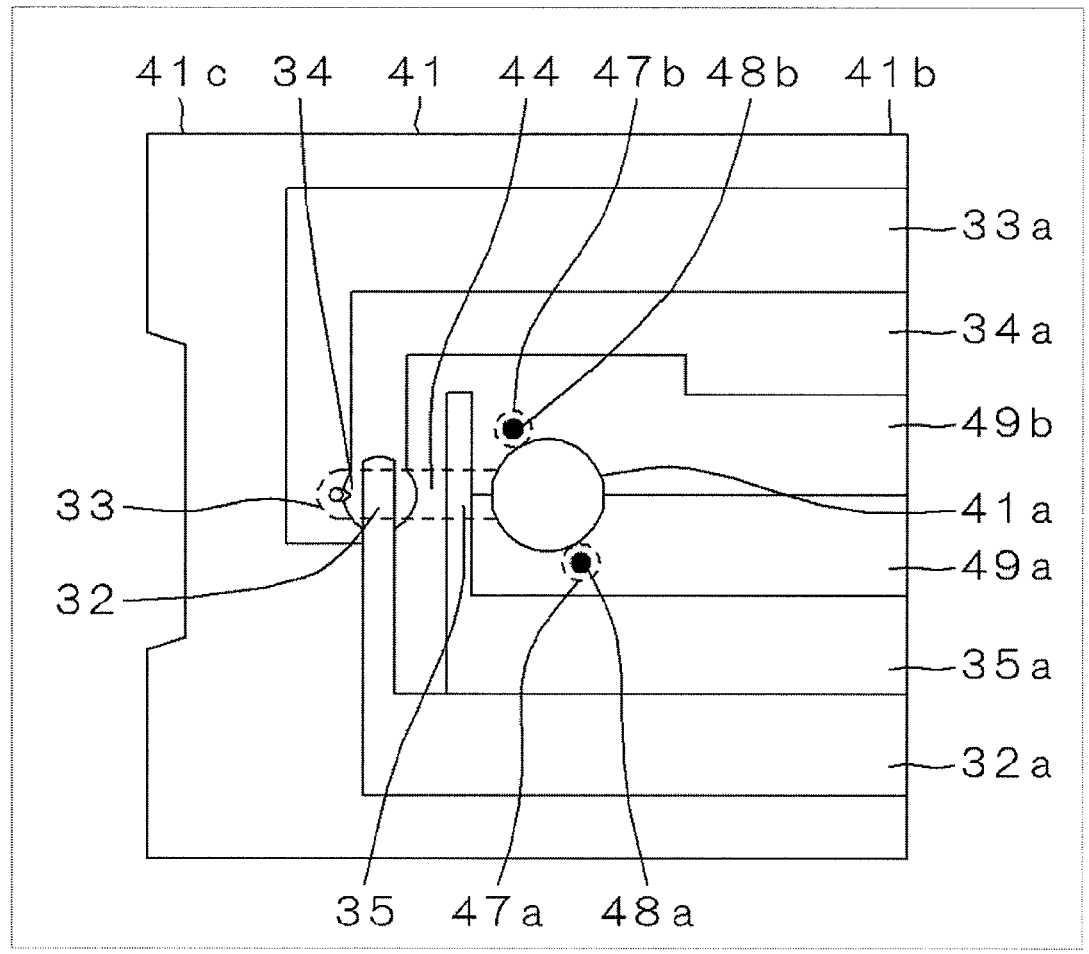
FIG. 5 is a plan view of a substrate constituting the sensor according to Embodiment 1 of the present invention.

FIG. 4 is a cross sectional view showing a sensor according to Embodiment 1 of the present invention and its neighborhood. FIG. 5 is a plan view of a substrate constituting the above-described sensor, and FIG. 6 is an exploded perspective view of the sensor.

Figure 6:
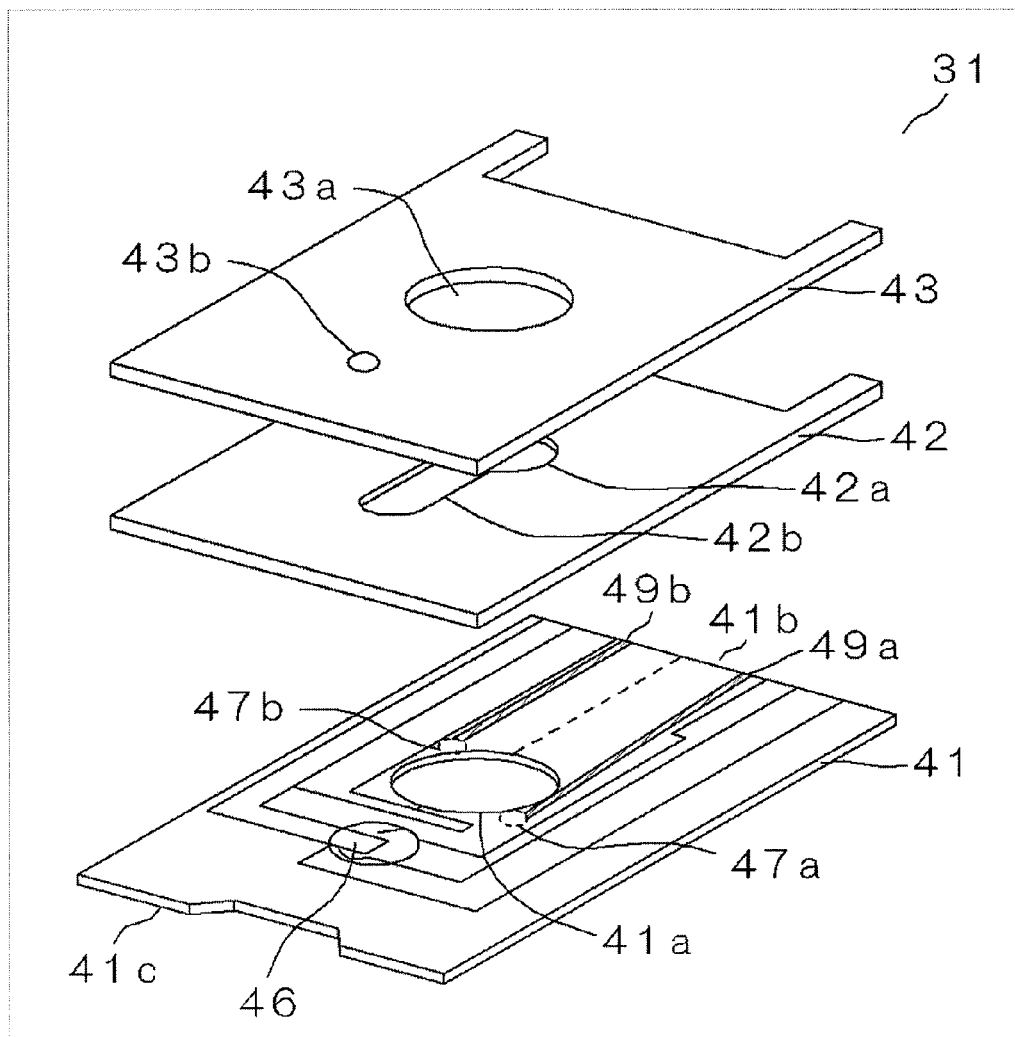
FIG. 6 is an exploded perspective view of the sensor according to Embodiment 1.

As shown in FIG. 4 to FIG. 6, sensor 30 has plate-like base body 31. Base body 31 has substrate 41 having an upper surface on which detection electrodes and connection electrodes (see FIG. 5) are provided; spacer 42 that is mounted on the upper surface side of substrate 41 and has slit 42b (see FIG. 6) formed inside to constitute part of supply path 44; and cover 43 mounted on the upper surface side of spacer 42.

Storing section 45 penetrating base body 31 is provided in approximately the center of base body 31. Supply path 44 coupled to storing section 45 to introduce blood 16 (see FIG. 8) is formed. One side of supply path 44 is coupled to air hole 43b provided in cover 43. In addition, detecting section 46 that detects the properties of blood 16 is provided on the upper surface side of substrate 41 forming the lower surface of supply path 44.

Skin detecting electrodes 47a and 47b that detect contact with skin 15 are formed in the vicinity of storing section 45 on the lower surface of substrate 41 and guided to the upper surface side of substrate 41 through conductors 48a and 48b, respectively. Skin detecting electrodes 47a and 47b preferably project from the lower surface of substrate 41 toward the skin 15 side. In addition, skin detecting electrodes 47a and 47b preferably have a convex shape projecting 0.3 to 5 mm. Moreover, skin detecting electrodes 47a and 47b preferably project 0.5 to 2 mm. When the patient contacts the lower surface of substrate 41 with skin 15, skin 15 closes one side of storing section 45 and certainly contacts skin detecting electrodes 47a and 47b.

[Skin Detecting Electrodes 47a and 47b, and Skin Detecting Sensor 47]

Skin detecting sensor 47, a skin detecting section, is composed of the above-described skin detecting electrodes 47a and 47b. Skin detecting sensor 47 detects contact with skin 15 by measuring electrical conduction (e.g. electrical resistance) between skin detecting electrode 47a and skin detecting electrode 47b. Here, the above-described "electrical conduction" is detected by measuring impedance. Measurement of electrical resistance is a typical impedance measurement. The measurement circuit in sensor 30 will be described in detail with Embodiment 6.

With the present embodiment, skin detecting sensor 47 performs detection by electrodes. The reason of this is that, currently, detection using electrodes allows apparatuses to be compact and provided at low cost. Here, skin detecting sensor 47 is not limited to detection using electrodes, and it is equally possible to use a piezo-electric sensor, an optical sensor using reflected light, a mechanical contact, an infrared sensor and so forth. Here, this is the same in the following embodiments.

[Detection electrodes 32 to 35]

Supply path 44 is a guide path that guides blood 16 stored in storing section 45 into detecting section 46 at a breath and a controlled speed by capillary action. The capacity of supply path 44 is 0.1 to 3 μL. Meanwhile, the capacity of storing section 45 is 1 to 10 μL. Preferably, the capacity of supply path 44 is 0.1 to 0.5 μL, and the capacity of storing section 45 is 1 to 3 μL.

Reagent 50 is placed on detecting section 46. This reagent 50 is formed by adding and dissolving PQQ-GDH (0.1 to 5.0 U/sensor), potassium ferricyanide (10 to 200 millimoles), maltitol (1 to 50 millimoles) and taurine (20 to 200 millimoles) in a CMC solution of 0.01 to 2.0 wt % to prepare a reagent solution, by dropping the reagent solution on detection electrodes 32 and 34 (see FIG. 5) formed on substrate 41 and drying.

In addition, polyethylene terephthalate (PET) is used as the material for substrate 41, spacer 42 and cover 43. By this means, the maintenance cost is reduced by using the same material.

FIG. 5 is a plan view of substrate 41. Connection electrodes 32a to 35a and connection electrodes 49a and 49b connected to skin detecting electrodes 47a and 47b constituting the skin detecting section are formed in one end 41b of substrate 41. In addition, detection electrode 35 connected to connection electrode 35a, detection electrode 34 connected to connection electrode 34a, detection electrode 32 connected to connection electrode 32a and detection electrode 33 connected to connection electrode 33a are provided in order from substrate hole 41a toward the other end 41c of substrate 41.

These detection electrodes 32 to 35 are provided on the lower surface of supply path 44 (see FIG. 4) provided in spacer 42. In addition, there is detecting section 46 (see FIG. 6) on detection electrodes 32 and 33, and reagent 50 is placed on detecting section 46.

An electrically conductive layer is formed on the upper surface of substrate 41 by the sputtering method or the vapor deposition method using materials such as gold, platinum, or palladium. Then, detection electrodes 32 to 35, connection electrodes 32a to 35a respectively drawn from these detection electrodes 32 to 35 and connection electrodes 49a and 49b are integrally formed by using laser machining on the electrically conductive layer formed. Connection electrodes 49a and 49b are connected to skin detecting electrodes 47a and 47b through conductors 48a and 48b (see FIG. 4).

As shown in FIG. 6, detection electrodes 32 to 35, connection electrodes 33a to 35a for detection electrodes 32 to 35 and connection electrodes 49a and 49b for skin detecting electrodes 47a and 47b are provided on the upper surface of substrate 41. In addition, spacer 42 in which slit 42b is formed is mounted on the upper surfaces of these detection electrodes 32 to 35, and further, cover 43 is mounted on the upper surface of this spacer 42.

Substrate hole 41a is provided in approximately the center of substrate 41, and spacer hole 42a is provided in approximately the center of spacer 42 so as to communicate with this substrate hole 41a. In addition, cover hole 43a is provided in approximately the center of cover 43 so as to communicate with this spacer hole 42a. Moreover, air hole 43b linked to one side of slit 42b formed in spacer 42 is provided in cover 43.

In addition, the other side of slit 42b is connected to spacer 42a.

Next, detection electrodes 32 to 35 that analyze components in a blood sample will be explained.

The above-described electrodes 32 to 35 represent an electrode system that analyzes components in a blood sample. Detection electrodes 32 to 35 are composed of working electrodes and counter electrodes and measure the current value by oxidation-reduction between the counter electrodes and the working electrodes to determine the quantity of the substrate. That is, the quantity of a target substance is determined by arranging working electrodes and counter electrodes at regular intervals to contact reduced electron carriers resulting from a specific reaction between the target substance and enzyme, applying a voltage between these working electrodes and counter electrodes for a certain period of time to oxidize the reduced electron carriers and measuring the current value (waveform) obtained thereupon.

Here, when working electrodes are indicated as positive electrodes and counter electrodes are indicated as negative electrodes, the above-described oxidant is a substance that electrochemically reduces in positive electrodes in a case in which a voltage equal to or lower than 3.0 V is applied. As oxidant, reversible electron-activated compounds, such as ferricyanide, p-benzoquinone, p-benzoquinone derivatives, oxidized phenazine methosulfate, methylene blue, ferricinium and ferricinium derivatives, are used as examples. A preferable oxidant is ferricyanide. Preferable ferricyanide is potassium ferricyanide.

Glucose oxidase, glucose dehydrogenase, lactate oxidase, lactate dehydrogenase, bilirubin oxidase and cholesterol oxidase are examples of oxidation-reduction enzymes.

Although, with the present embodiment, a substance other than blood cells, such as glucose, is used as an example of a substance to be analyzed in a blood sample, the present invention is naturally applicable to measurement of other substances to be analyzed, such as albumin, lactic acid, bilirubin and cholesterol. The oxidation-reduction enzyme to use has its own substrate that is a substance to be analyzed.

Here, one ends of the above-described detection electrodes 32 to 35 are exposed to the outside through connection terminals (leads). In addition, working electrodes, counter electrodes, detection electrodes and Hct electrodes serving as detecting electrodes to analyze components in a blood sample are coupled to leads (not shown) individually. One end of each lead is exposed to the outside of the sensor in the end part of the insulating substrate not covered with the spacer and the cover so as to apply a voltage between electrodes.

[Arrangement of Skin Detecting Sensor 47 and Detection Electrodes 32 to 35]

As shown in FIG. 4 to FIG. 6, skin detecting sensor 47 composed of skin detecting electrodes 47a and skin detecting electrode 47b and a blood component measurement means composed of detection electrodes 32 to 35 are provided in substrate 31 as separate parts in plate-like base body 31. This arrangement is merely an example and is by no means limiting. As the present embodiment, skin detecting electrodes 47a and 47b are preferably mounted in the blood supply side. In addition, skin detecting electrodes 47a and 47b are preferably arranged in the vicinity of blood storing section 45 provided in approximately the center or the end part (Embodiment 5 described later) of base body 31. By this arrangement, it is possible to more accurately detect skin in the puncturing position.

Figure 7A:
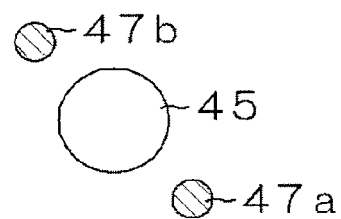
FIG. 7A is a plan view of primary parts showing an exemplary arrangement of a skin detecting sensor in the sensor according to Embodiment 1.
Figure 7B:
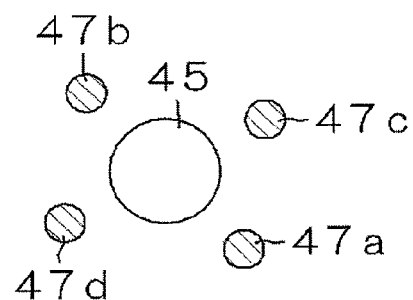
FIG. 7B is a plan view of primary parts showing an exemplary arrangement of a skin detecting sensor in the sensor according to Embodiment 1.
Figure 7C:
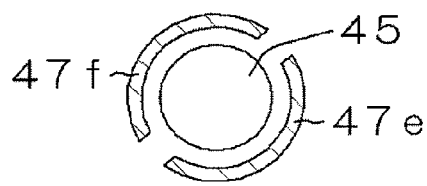
FIG. 7C is a plan view of primary parts showing an exemplary arrangement of a skin detecting sensor in the sensor according to Embodiment 1.
Figure 7D:
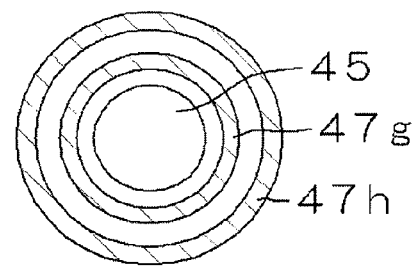
FIG. 7D is a plan view of primary parts showing an exemplary arrangement of a skin detecting sensor in the sensor according to Embodiment 1.

FIG. 7A to FIG. 7D are plan views of primary parts showing various exemplary arrangements of the above-described skin detecting sensor 47. FIG. 7A shows a first example, FIG. 7B shows a second example, FIG. 7C shows a third example and FIG. 7D shows a fourth example. Here, skin detecting sensor 47 described herein is applicable to the following embodiments.

FIG. 7A shows a configuration in which two skin detecting electrodes 47a and 47b, constituting skin detecting sensor 47 sandwich storing section 45 to face one another. These skin detecting electrodes 47a and 47b are guided to the upper surface side of substrate 41 through conductors 48a and 48b, respectively, and connected with connection electrodes 49a and 49b. The skin detecting sensor shown in FIG. 7A has a simple configuration with two skin detecting electrodes 47a and 47b, so that it is easily manufactured.

FIG. 7B shows a configuration in which four skin detecting electrodes 47a to 47d, constituting skin detecting sensor 47, sandwich storing section 45 to face each other. These skin detecting electrodes 47a to 47d are guided to the upper surface side of substrate 41 through conductors 48a to 48d, respectively. On the upper surface side of substrate 41, conductor 48a and conductor 48b are connected one another and connected to connection electrode 49a, and also conductor 48c (not shown) and conductor 48d (not shown) are connected one another and connected to connection electrode 49b. By the configuration shown in FIG. 7B, the reliability of contact with skin 15 is improved compared to the configuration shown in FIG. 7A.

FIG. 7C shows a configuration in which two semicircular skin detecting electrodes 47e and 47f constituting skin detecting sensor 47 sandwich storing section 45 to face one another. Skin detecting electrodes 47e and 47f are guided to the upper surface side of substrate 41 through conductors 48a and 48b and connected to connection electrodes 49a and 49b, respectively. This configuration has a feature to allow a reduction in contact resistance and to allow easier detection of skin because the contact area with skin 15 is larger than those in the two preceding examples. Generally, the electric resistance of skin 15 is 20 K ohm to 3000 K ohm per centimeter when skin 15 is dry.

FIG. 7D shows a configuration in which two concentric skin detecting electrodes 47g and 47h constituting skin detecting sensor 47 are arranged around storing section 45. Skin detecting electrodes 47g and 47h are guided to the upper surface of substrate 41 through conductors 48a and 48b, and connected to connection electrodes 49a and 49b, respectively. This configuration has a feature to allow detection when skin 15 is located in the vicinity of storing section 45.

Figure 8:
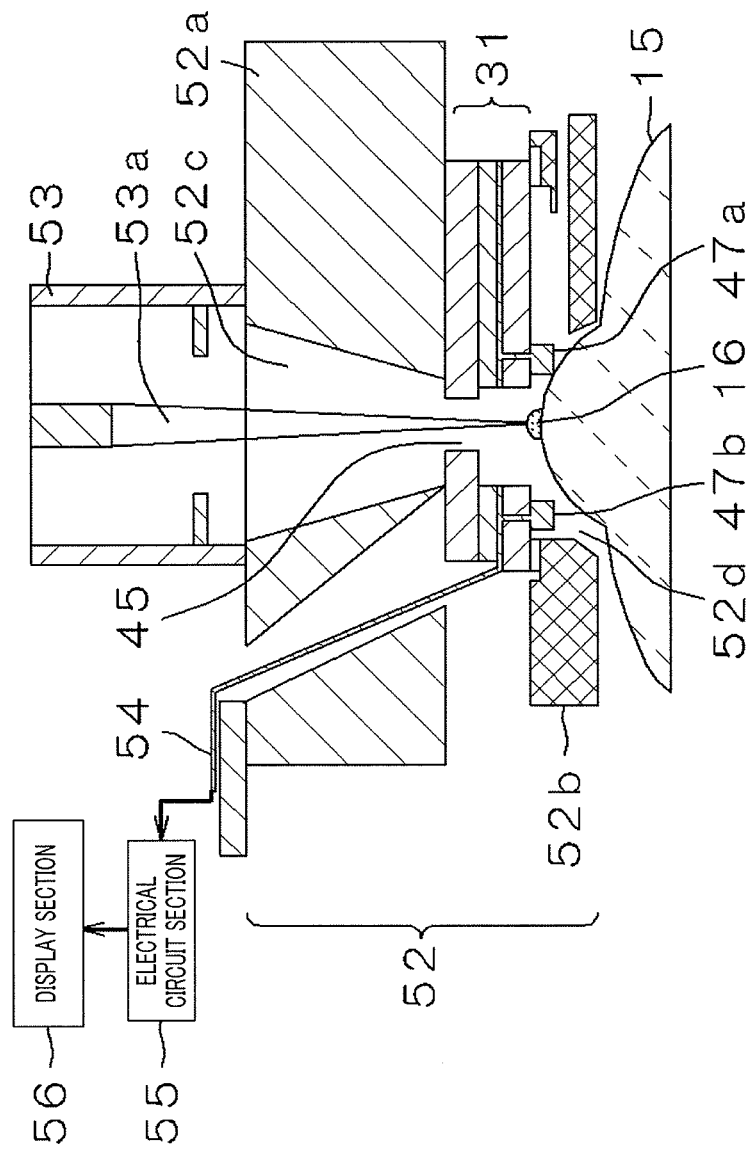
FIG. 8 is a cross sectional view showing the primary part around a puncturing section and its neighborhood in a blood test apparatus according to Embodiment 1.

FIG. 8 is a cross sectional view showing the primary part around the puncturing section and its neighborhood in a blood test apparatus.

As shown in FIG. 8, puncturing section 52 is composed of upper holder 52a and lower holder 52b. Sensor 30 (although base body 31 is shown in FIG. 8, it is used synonymously with sensor 30) is sandwiched and fixed between upper holder 52a and lower holder 52b.

Laser puncturing unit (used as an example of puncturing means) 53 (partially shown) is fixedly provided above puncturing section 52 and emits laser light 53a. Here, as a puncturing means, a needle puncturing unit that punctures skin 15 using a puncture needle may be used.

Through hole 52c is provided in upper holder 52a and also through hole 52d is provided in lower holder 52b. When sensor 30 is sandwiched and fixed between upper holder 52a and lower holder 52b, through hole 52c, storing section 45 and through hole 52d are arranged on a straight line. Laser light 53a penetrates through hole 52c, storing section 45 and through hole 52d arranged on a straight line and punctures skin 15.

In addition, connector 54 contacting connection electrodes 32a to 35a corresponding to detection electrodes 32 to 35 and connection electrodes 49a and 49b corresponding to skin detecting electrodes 47a and 47b (described later) formed in sensor 30 is mounted in upper holder 52a. This connector 54 is connected to electrical circuit section 55. In addition, the output of electrical circuit section 55 is connected to display section 56.

Skin detecting electrodes 47a and 47b are provided in sensor 30 and constitute skin detecting sensor 47, which is a skin detecting section. Outputs from skin detecting electrodes 47a and 47b are connected to electrical circuit section 55 through connection electrodes 49a and 49b, and connector 54. Here, processing of signals outputted from sensor 30 and the measurement circuit in sensor 30 will be described in detail with Embodiment 6.

As described above in detail, according to the present embodiment, skin detecting electrodes 47a and 47b that detect contact with skin 15 and conductors 48a and 48b that guide skin detecting electrodes 47a and 47b to the outside are formed in the vicinity of storing section 45 on the lower surface of substrate 41 in sensor 30 and connection electrodes 49a and 49b are also formed in sensor 30. By this means, the detecting section to detect contact with skin is provided in a position located closest to the puncturing position, in sensor 30, so that it is possible to check that skin certainly contacts the interior of the storing section or the vicinity of the storing section, and therefore to improve the reliability.

In addition, it is possible to prevent the interior of the apparatus body from being stained, so that it is possible to provide sanitation and prevent a risk of infection. Moreover, maintenance is not necessary, so that it is possible to reduce the trouble and cost. A new sensor is provided every time the apparatus is used, so that deterioration in the accuracy of detection due to stains and so forth is prevented.

As described above, skin detecting electrodes 47a and 47b constituting skin detecting sensor 47, which is a skin detecting section, are provided in the vicinity of storing section 45, so that it is possible to check that skin 15 contacts the vicinity of storing section 45. Therefore, entire blood 16 exuding from skin 15 flows into storing section 45 without flowing outside. That is, it is possible to make good use of exuding blood 16. This allows electrical circuit section 55 in blood test apparatus 101 (see FIG. 20) side to reliably and accurately measure blood 16. The test value of this measured blood 16 is displayed on display section 56.

In addition, since skin detecting electrodes 47a and 47b are provided in the sensor 30 side, these skin detecting electrodes 47a and 47b are replaced every time a series of puncturing, measurement and test is performed, so that sanitation is provided. Moreover, it is possible to maintain the accuracy and make maintenance easy.

Embodiment 2

Figure 9:
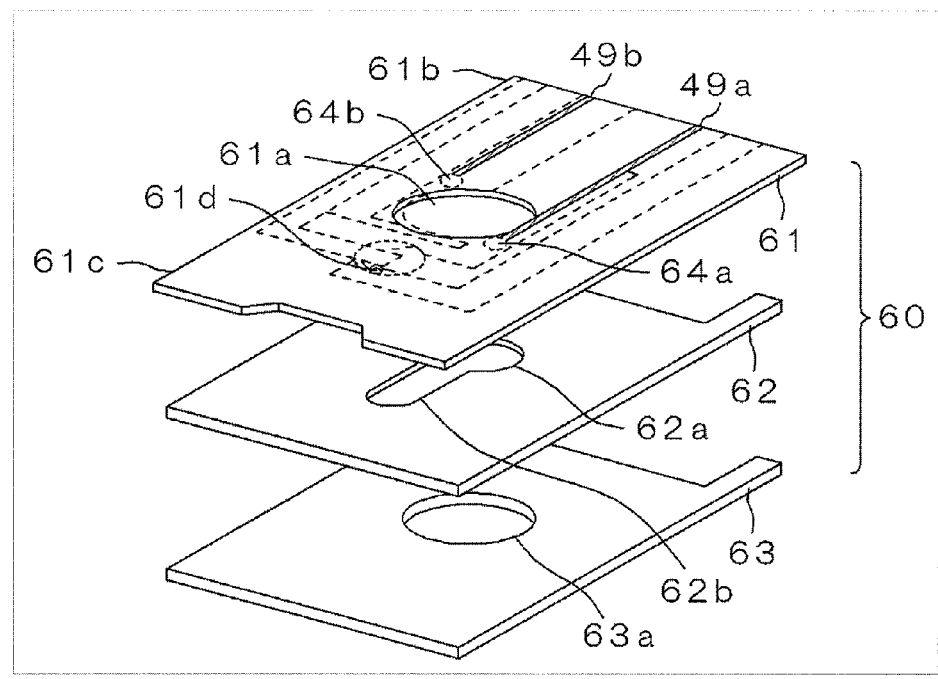
FIG. 9 is an exploded perspective view of the sensor according to Embodiment 2 of the present invention.
Figure 10:
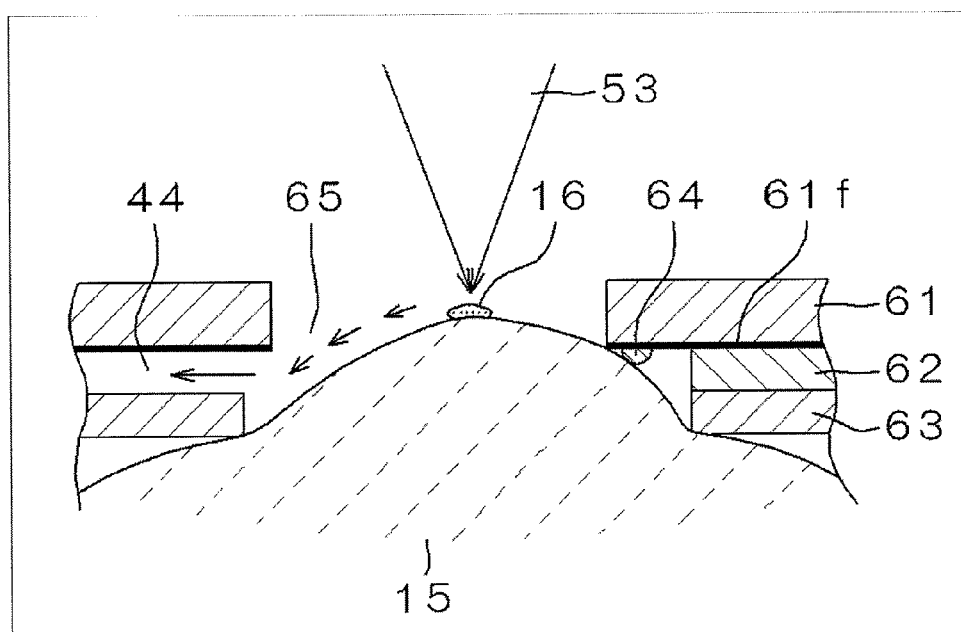
FIG. 10 is a cross sectional view of the sensor according to Embodiment 2 and its neighboring primary parts.

FIG. 9 is an exploded perspective view of a sensor according to Embodiment 2 of the present invention. FIG. 10 is a cross sectional view showing the above-described sensor and its neighboring primary parts.

Sensor 60 explained with Embodiment 2 differs from sensor 30 explained with Embodiment 1 in that the sensor is turned upside down and in that the configuration of storing section 65 (see FIG. 10) varies. Here, the same components as in Embodiment 1 will be assigned the same reference numerals, so that descriptions will be simplified. This will be the same in the following embodiments.

As shown in FIG. 9, detection electrodes 32 to 35 that detect components of blood and skin detecting section 64a and 64b constituting a skin detecting section are formed on the lower surface of substrate 61 (corresponding to substrate 41 in Embodiment 1). In one end 61b of substrate 61, connection electrodes 32a to 35a respectively corresponding to detecting electrodes 32 to 35 and connection electrodes 49a and 49b respectively corresponding to skin detecting electrodes 64a and 64b are provided. In addition, in the other end 61c side of substrate 61, air hole 61d coupled to supply path 44 is provided.

Spacer 62 (corresponding to spacer 42 in Embodiment 1) in which slit 62b (corresponding to slit 42b in Embodiment 1) constituting supply path 44 (see FIG. 4) is formed, is mounted on the lower surface side of substrate 61. Cover 63, which is able to contact skin 15, is mounted on the lower surface side of this spacer 62.

In addition, substrate hole 61a formed in approximately the center of substrate 61, spacer hole 62a formed in approximately the center of spacer 62 and cover hole 63a formed in approximately the center of cover 63 communicate with each other to form storing section 65 (see FIG. 10).

With the present embodiment, the substrate and the cover are turned upside down compared to sensor 30 in Embodiment 1, and therefore, skin detecting electrodes 64a and 64b are provided on the lower surface side of substrate 61, that is, provided in the skin side, and therefore, are able to directly contact skin 15. Therefore, conductors 48a and 48b to electrically connect the upper surface and the lower surface of the substrate as described with Embodiment 1 are not required. This feature allows a simpler configuration, easier manufacturing and a lower cost than those in Embodiment 1.

In addition, as shown in FIG. 10, the diameter of substrate hole 61a forming storing section 65 (corresponding to storing section 45 in Embodiment 1) is smaller than the diameter of spacer hole 62a (corresponding to spacer hole 42a in Embodiment 1) and the diameter of cover hole 63a (corresponding to cover hole 43a in Embodiment 1). By this means, site 61f between small substrate hole 61a and large spacer hole 62a and cover hole 63a is formed in storing section 65 and it is possible to provide skin detecting electrodes 64a and 64b, which are able to contact skin 15, in this site 61f.

Laser light 53a penetrates storing section 65 configured as described above and punctures skin 15. Blood 16 exudes from punctured skin 15. Exuding blood 16 flows into supply path 44 at a constant speed.

Here, processing of signals outputted from sensor 60 and the measurement circuit in sensor 60 will be described in detail with Embodiment 6.

Figure 11A:
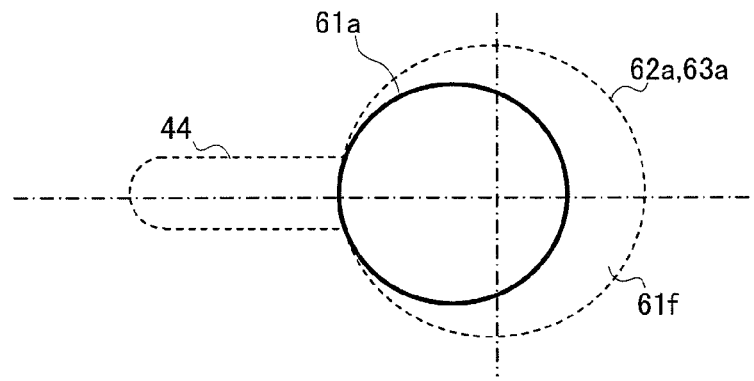
FIG. 11A is a plan view of primary parts explaining a position in which a substrate hole is formed in the blood test apparatus according to Embodiment 2.
Figure 11B:
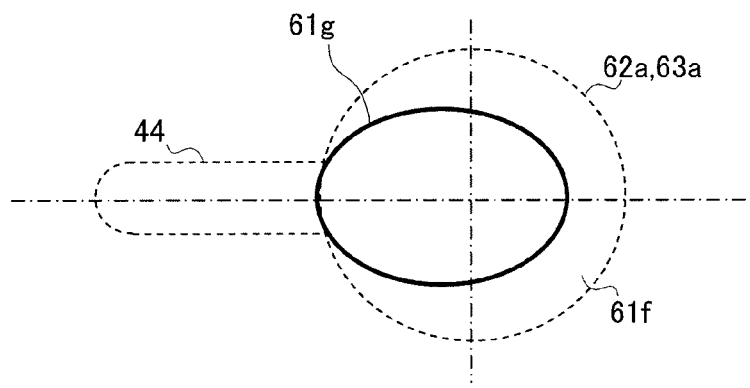
FIG. 11B is a plan view of primary parts explaining a position in which a substrate hole is formed in the blood test apparatus according to Embodiment 2.

FIG. 11A and FIG. 11B are plan views of primary parts explaining forming positions of substrate hole 61a. FIG. 11A shows the first example and FIG. 11B shows a second example.

In FIG. 11A, substrate hole 61a has a circular shape and is arranged in a position shifted from the center of spacer hole 62a and cover hole 63a to the supply path 44 side. By this means, exuding blood 16 easily flows into supply path 44 and it is possible to provide large site 61f in which skin detecting electrodes 64a and 64b are formed. Therefore, contact with skin 15 is easily allowed and it is possible to increase the reliability of skin detection.

In FIG. 11B, substrate hole 61g (corresponding to substrate hole 61a and a variation of substrate hole 61a) has an elliptical shape longer in the direction of the supply path 44 side and is arranged in a position shifted from the center of spacer hole 62a and cover hole 63a to the supply path 44 side. By this means, exuding blood 16 more easily flows into supply path 44, and it is possible to make site 61f larger to form skin detecting electrodes 64a and 64b. Contact with skin 15 is further easier, and it is possible to improve the reliability of skin detection in the same way as in FIG. 11A.

In addition, although FIG. 11 shows a case in which the shape of the substrate hole is a circle and a semicircle, the present embodiment is not limited to this. A polygon is possible, and substrate hole 61a or 61g, spacer hole 62a and cover hole 63a may have similar shapes to each other. Naturally, the shapes of hole 61a, 62a and 63a may differ from each other. It is possible to obtain the same effect as in FIG. 11 by arranging each hole 61a, 62a and 63a in a position shifted from its center to the supply path 44 side in the same way as substrate hole 61a or 61g.

Embodiment 3

Figure 12:
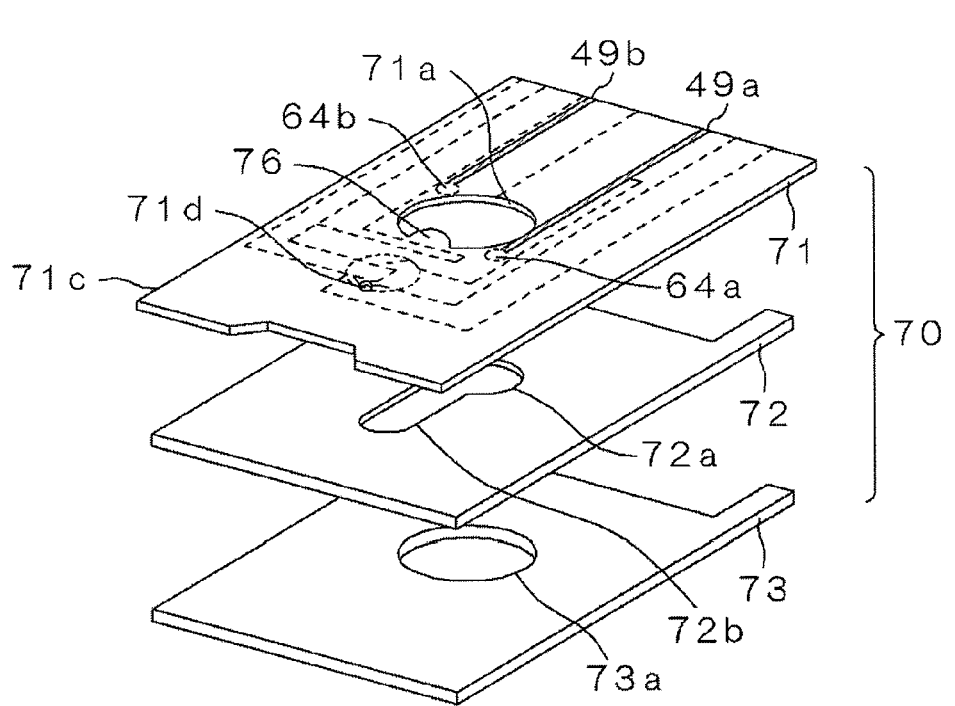
FIG. 12 is an exploded perspective view of a sensor according to Embodiment 3 of the present invention.
Figure 13:
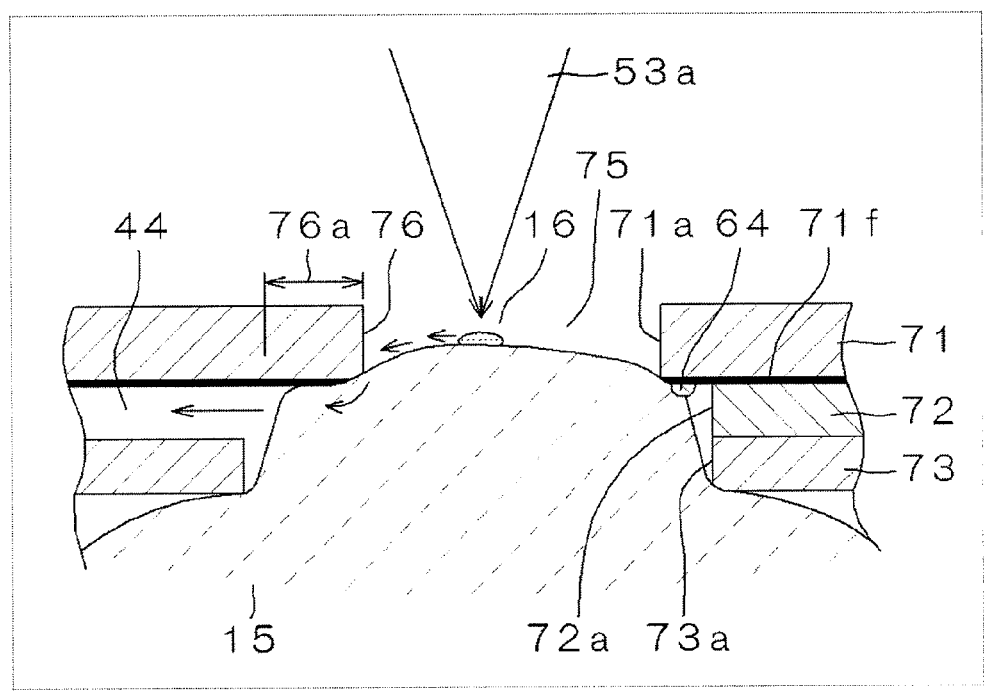
FIG. 13 is cross sectional view showing the sensor according to Embodiment 3 and its neighboring primary parts.
Figure 14:
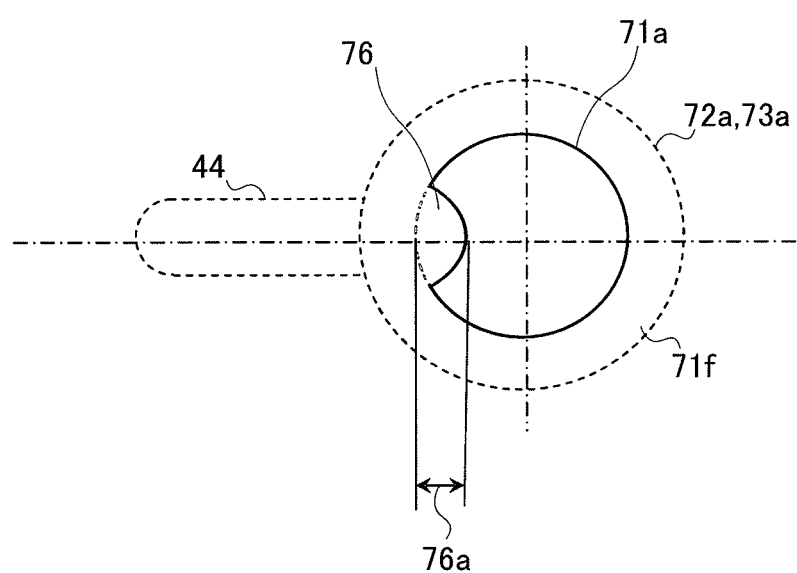
FIG. 14 is a plan view showing primary parts of the sensor according to Embodiment 3.

FIG. 12 is an exploded perspective view of a sensor according to Embodiment 3. FIG. 13 is a cross sectional view showing the above-described sensor and its neighboring primary parts, and FIG. 14 is a cross sectional view showing primary parts of the above-described sensor.

Sensor 70 explained with Embodiment 3 differs from sensor 30 explained in Embodiment 1 in that the sensor is turned upside down and in that a convex part projecting from the supply path side to the center of the substrate hole is formed.

As shown in FIG. 12, detection electrodes 32 to 35, skin detecting electrodes 64a and 64b, connection electrodes 32a and 35a and connection electrodes 49a and 49b are provided on the lower surface of substrate 71 (corresponding to substrate 41 in Embodiment 1). Air hole 71d coupled to supply path 44 is provided in one end 71c side of substrate 71. Moreover, convex part 76 projecting to the center of substrate hole 71a is formed in the supply path 44 side of substrate hole 71a (corresponding to substrate hole 41a in Embodiment 1).

Spacer 72 (corresponding to spacer 42 in Embodiment 1) in which slit 72b (corresponding to slit 42b in Embodiment 1) constituting supply path 44 is formed, is mounted on the lower surface side of substrate 71. Cover 73 (corresponding to cover 63 in Embodiment 2) to contact skin 15 is mounted on the lower surface side of spacer 72 is mounted on the lower surface side of this spacer 72.

In addition, substrate hole 71a formed in approximately the center of substrate 71, spacer hole 72a (corresponding to spacer hole 42a in Embodiment 1) formed in approximately the center of spacer 72 and cover hole 73a (corresponding to cover hole 43a in Embodiment 1) formed in approximately the center of cover 73 communicate with each other to form storing section 75 (corresponding to storing section 45 in Embodiment 1).

With the present embodiment, the sensor is turned upside down compared to sensor 30 in Embodiment 1, so that skin detecting electrodes 64a and 64b directly contact skin 15. Therefore, conductors 48a and 48b to electrically connect the upper surface and the lower surface of the substrate as described with Embodiment 1 are not required. This feature allows a simpler configuration, easier manufacturing and a lower cost than those in Embodiment 1.

In addition, as shown in FIG. 13, the diameter of substrate hole 71a forming storing section 75 is smaller than the diameter of spacer hole 72a and the diameter of cover hole 73a. By this means, site 71f between small substrate hole 71a and large spacer hole 72a and cover hole 73a is formed in storing section 75. It is possible to provide skin detecting electrodes 64a and 64b, which are able to contact skin 15, in this site 71f.

In addition, convex part 76 having interval 76a and projecting is formed in the supply path 44 side of substrate hole 71a. The inlet of supply path 44 is not blocked with skin 15 thanks to the effect of convex part 76. By this means, when laser light 53a punctures skin 15, it is possible to make exuding blood 16 easily flow from the substrate hole 71a side into supply path 44.

In addition, the diameter of substrate hole 71a forming storing section 75 is smaller than the diameter of spacer hole 72a and the diameter of cover hole 73a. By this means, site 71f between small substrate hole 71a and large spacer hole 72a and cover hole 73a is formed in storing section 75. It is possible to provide skin detecting electrodes 64a and 64b, which are able to contact skin 15, in this site 71f.

In addition, convex part 76 having interval 76a and projecting is formed in the supply path 44 side of substrate hole 71a. The inlet of supply path 44 is not closed with skin 15 thanks to the effect of convex part 76. By this means, when laser light 53a punctures skin 15, it is possible to make exuding blood 16 easily flow from the substrate hole 71a side into supply path 44.

Embodiment 4

Figure 15:
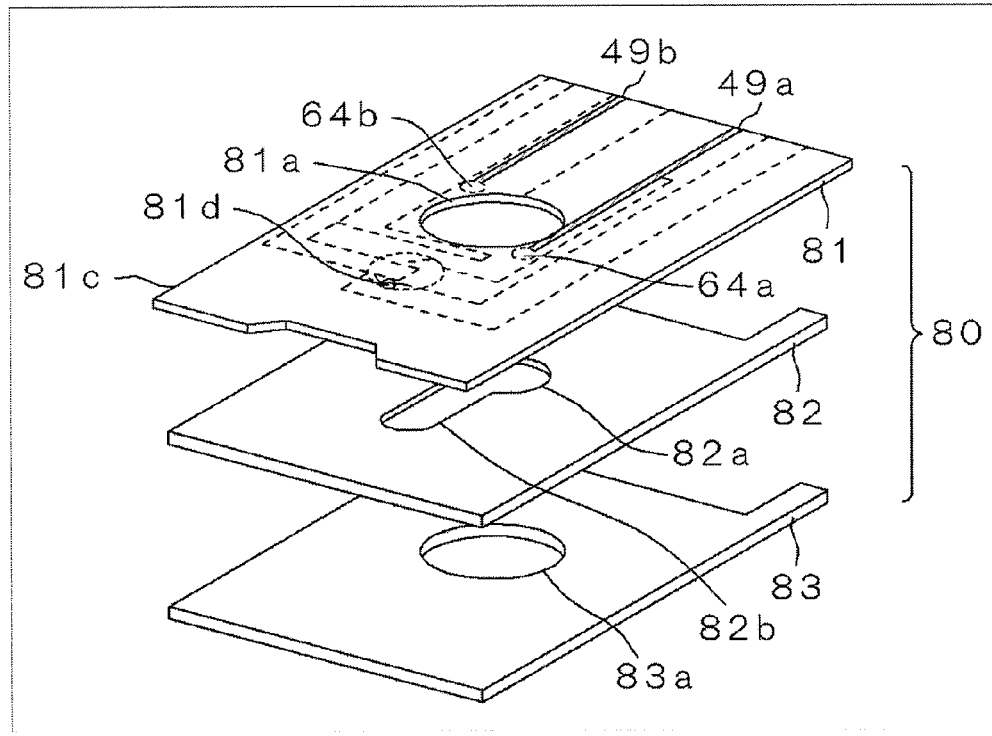
FIG. 15 is an exploded perspective view of a sensor according to Embodiment 4 of the present invention.
Figure 16:
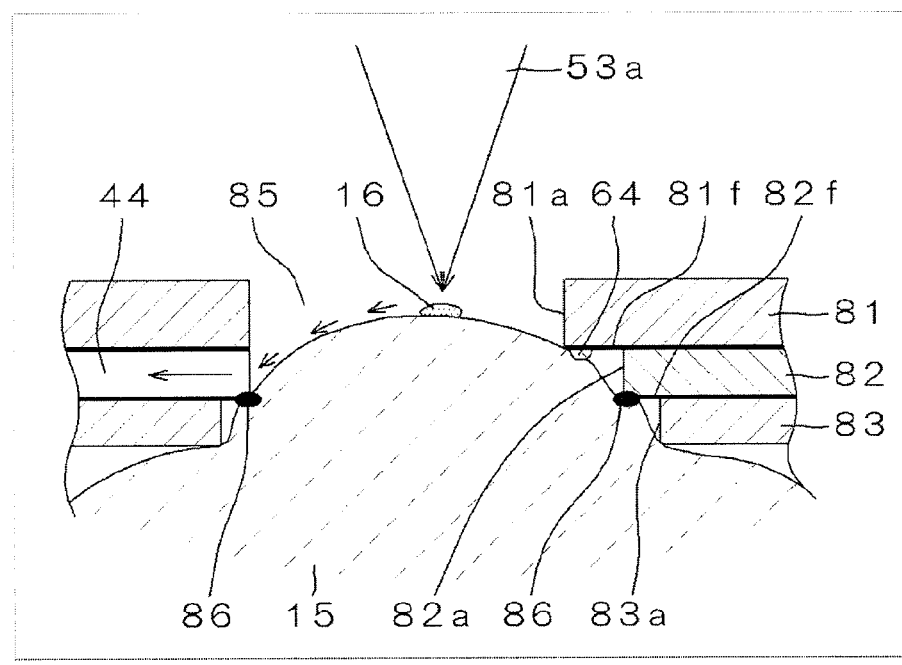
FIG. 16 is a cross sectional view showing the sensor according to Embodiment 4 and its neighboring primary parts.

FIG. 15 is an exploded perspective view of a sensor according to Embodiment 4. FIG. 16 is a cross sectional view showing the above-described sensor and its neighboring primary parts.

Sensor 80 explained with Embodiment 4 differs from sensor 30 explained with Embodiment 1 in that the sensor is turned upside down and in that an elastic body is mounted on the lower surface side in the end part of a spacer hole provided in a spacer.

As shown in FIG. 15, detection electrodes 32 to 35, skin detecting electrodes 64a and 64b, connection electrodes 32a to 35a and connection electrodes 49a and 49b are provided on the lower surface side of substrate 81 (corresponding to substrate 41 in Embodiment 1). In addition, substrate hole 81a forming storing section 85 (corresponding to storing section 45 in Embodiment 1) is formed in approximately the center of substrate 81. Air hole 81d coupled to supply path 44 is provided in one end 81c side of substrate 81.

Spacer 82 (corresponding to spacer 42 in Embodiment 1) in which slit 82b (corresponding to slit 42b in Embodiment 1) constituting supply path 44 is formed, is mounted on the lower surface side of substrate 81. Spacer hole 82a forming storing section 85 is formed in approximately the center of spacer 82. In addition, cover 83 (corresponding to cover 63 in Embodiment 2) to contact skin 15 is mounted on the lower surface side of spacer 82. Cover hole 83a is formed in approximately the center of cover 83. This cover hole 83a, substrate hole 81a and spacer hole 82a communicate with each other to form storing section 85.

Here, the size relationship between the diameters of substrate hole 81a, spacer hole 82a and cover hole 83a will be described. The diameter of substrate hole 81a is the smallest, and the diameter of spacer hole 82a is equal to or greater than the diameter of substrate hole 81a and equal to or smaller than the diameter of cover hole 83a. In addition, the diameter of cover hole 83a is greater than the diameter of substrate hole 81a and the diameter of spacer hole 82a. Viscous elastic body 86 (see FIG. 16) is mounted on the lower surface side in the end part of spacer hole 82a (middle hole) having this relationship.

With the present embodiment, the sensor is turned upside down compared to sensor 30 in Embodiment 1, and this allows direct contact with skin detecting electrodes 64a and 64b with skin 15. Therefore, conductors 48a and 48b to electrically connect the upper surface and the lower surface of the substrate as described with Embodiment 1 are not required. This feature allows a simpler configuration, easier manufacturing and a lower cost than those in Embodiment 1.

In addition, as shown in FIG. 16, the diameter of substrate hole 81a (small hole) forming storing section 85 is smaller than the diameter of middle spacer hole 82a (corresponding to spacer hole 42a in Embodiment 1), and the diameter of spacer hole 82a is smaller than the diameter of large cover hole 83a (corresponding to cover hole 63a in Embodiment 2). By this means, site 81f allowed to contact skin 15 is formed between small substrate hole 81a and middle spacer hole 82a in storing section 85, and it is possible to provide skin detecting electrodes 64a and 64b in this site 81f.

In addition, site 82f is formed on the lower surface side in the end part of middle spacer hole 82a in storing section 85, and it is possible to mount elastic body 86 in this site 82f. By this means, when laser light 53a punctures skin 15, spacer 82 and skin 15 firmly adhere to one another thanks to the effect of elastic body 86. Therefore, exuding blood 16 is reliably guided to supply path 44 without leaking from the cover 83 side.

Embodiment 5

Figure 17:
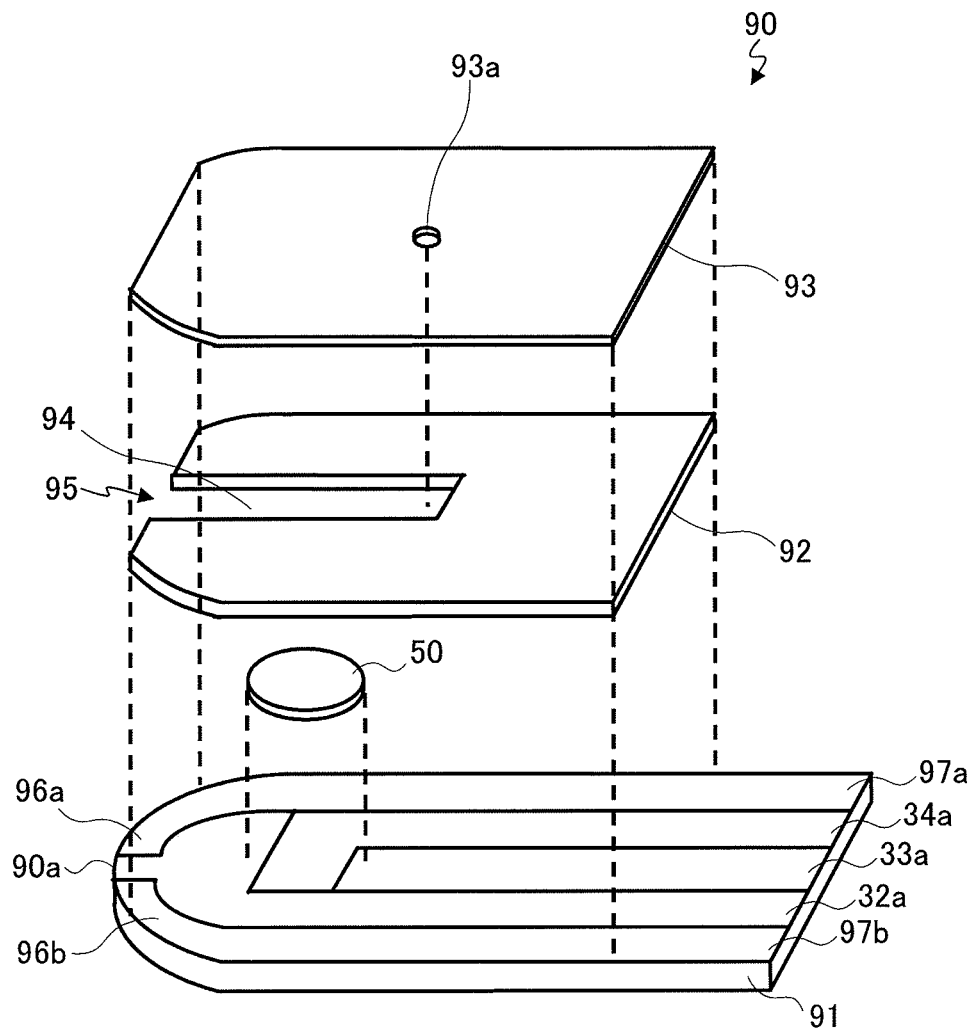
FIG. 17 is an exploded perspective view showing the assembly of a sensor according to Embodiment 5 of the present invention.
Figure 18:
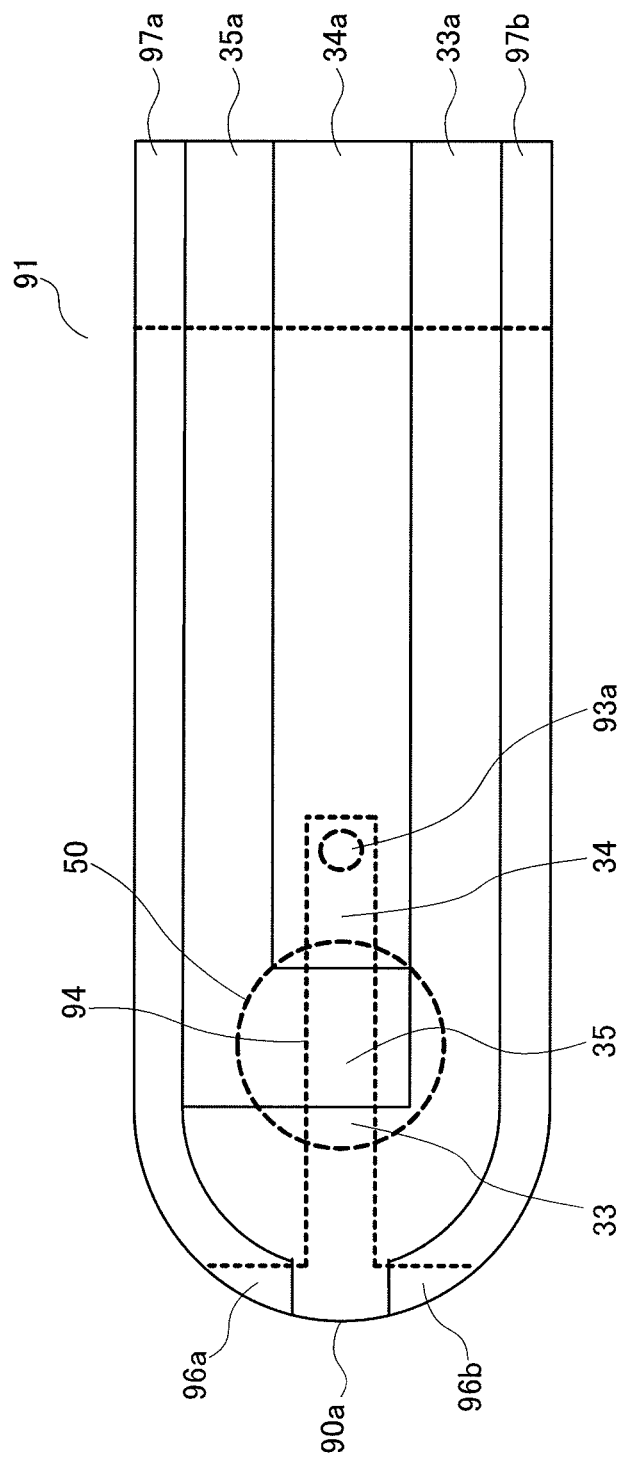
FIG. 18 is a plan view showing the sensor according to Embodiment 5.

FIG. 17 is an exploded perspective view showing an assembly of a sensor according to Embodiment 5 of the present invention. FIG. 18 is a plan view of the above-described sensor. The same components as in FIG. 4 will be assigned the same reference numerals.

As shown in FIG. 17, sensor 90 is configured to include substrate 91, reagent 50 placed on substrate 91, spacer 92 arranged to cover substrate 91 and reagent 50 and cover 93 arranged to cover spacer 92.

Storing section 95 is formed in one end 90a of sensor 90 by cutting part of spacer 92 to make blood supply path 94. Skin detecting electrodes 96a and 96b are formed in both sides of storing section 95 by exposing conductors without covering part of substrate 91 with spacer 92 and cover 93. In addition, air hole 93a is provided in cover 93, in a position to communicate with supply path 94.

As shown in FIG. 18, detection electrodes 33, 34 and 35, connection terminals 33a, 34a and 35a connected to detection electrodes 33, 34 and 35, respectively, and connection terminals 97a and 97b connected to skin detecting electrodes 96a and 96b, respectively, are formed on the upper surface of substrate 91.

Figure 19:
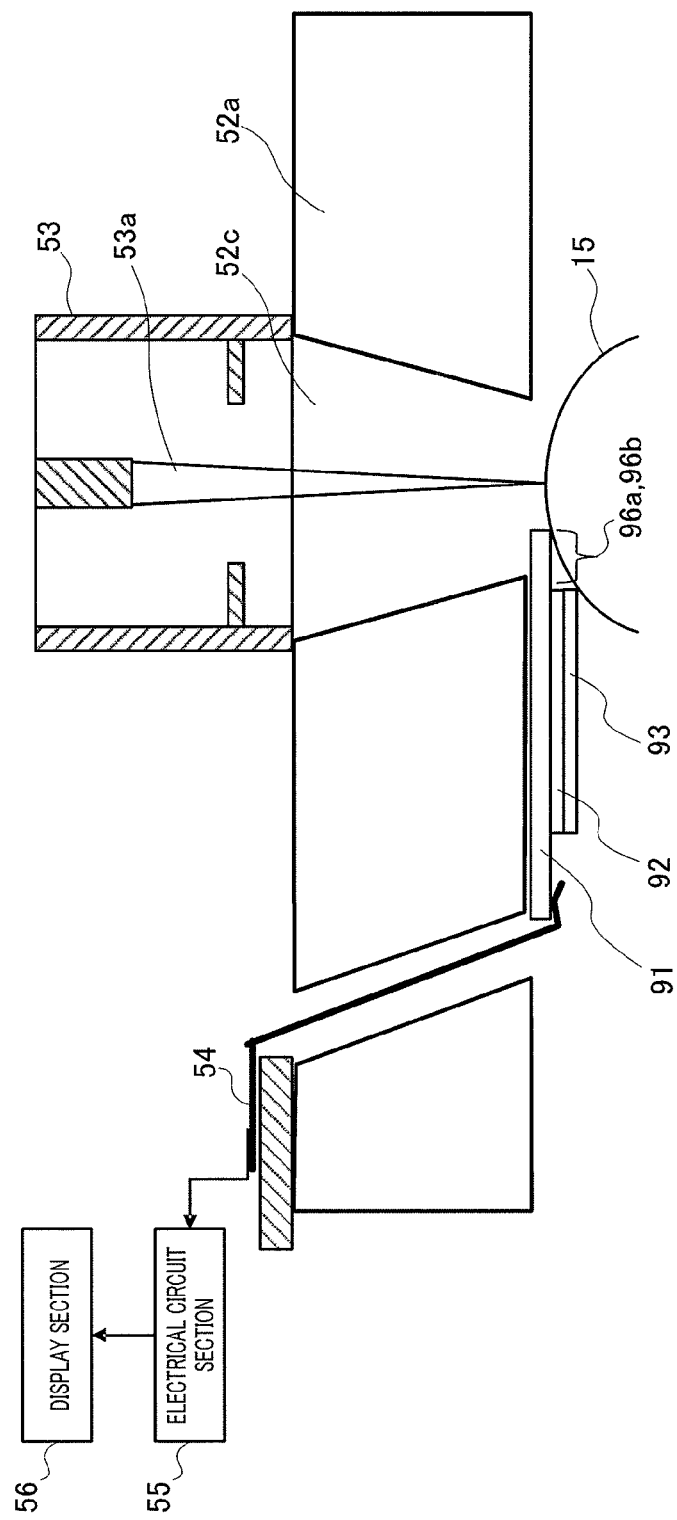
FIG. 19 is a cross sectional view showing the primary part around a puncturing section and its neighborhood in a blood test apparatus according to Embodiment 5.

FIG. 19 is a cross sectional view showing the primary part around a puncturing section in a blood test apparatus and its neighborhood. FIG. 19 corresponds to FIG. 8 of Embodiment 1.

As shown in FIG. 19, laser puncturing unit (used as an example of puncturing means) 53 (partially shown) is fixedly provided above upper holder 52a of puncturing section 52 and emits laser light 53a.

In addition, connector 54 contacting connection electrodes 97a and 97b (see FIG. 17 and FIG. 18) corresponding to skin detecting electrodes 96a and 96b is mounted in upper holder 52a and connected to electrical circuit section 55. In addition, the output of electrical circuit section 55 is connected to display section 56. Here, processing of signals outputted from sensor 90 and the measurement circuit in sensor 90 will be described in detail with Embodiment 6.

As compared to Embodiment 1 where hole-like blood storing section 45 is provided in approximately the center of sensor 30, blood storing section 95 is provided in end 90a of sensor 90 and blood 16 is dispensed to storing section 95 as drops in the present embodiment.

According to the present embodiment, the same skin detecting function as in Embodiment 1 is allowed even if blood storing section 95 is provided in end 90a of sensor 90.

Embodiment 6

With Embodiment 6, a blood test apparatus using sensor 30 explained with Embodiment 1 (this is not limited to sensor 30, and sensors 60, 70, 80 and 90 are possible) will be explained.

Figure 20:
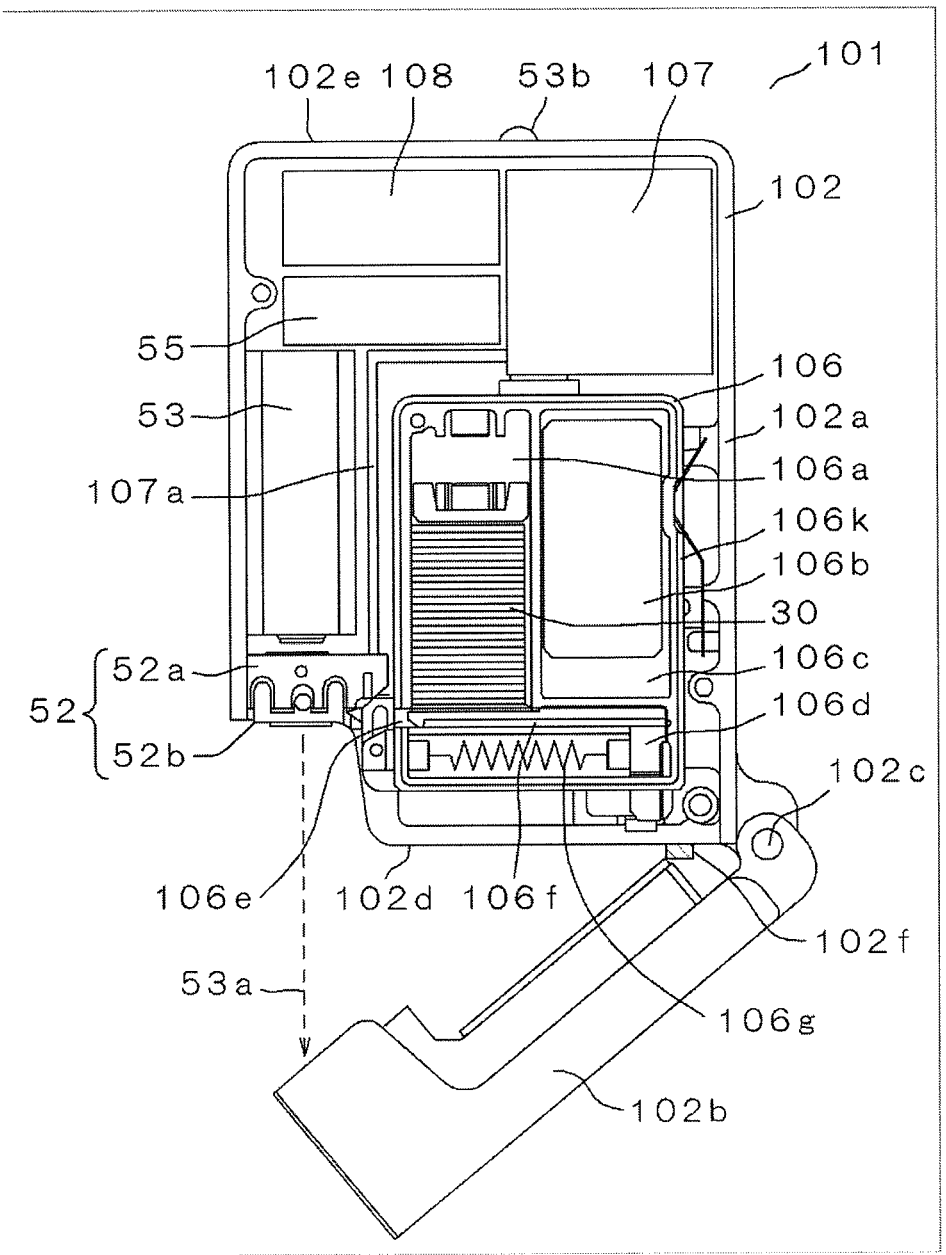
FIG. 20 is a cross sectional view showing a blood test apparatus according to Embodiment 6 of the present invention.

FIG. 20 is a cross sectional view of a blood test apparatus according to Embodiment 6.

As shown in FIG. 20, blood test apparatus 101 has housing 102 made of resin and having an approximately rectangular solid shape. Housing 102 is composed of main body 102a and cover 102b provided to pivotally move from main body 102a through supporting point 102c. Cover 102b is lockably provided to open at two angles, which are the first open angle of about 30 degrees and a second open angle of about 90 degrees. Open/close sensor 102f is mounted on lower edge 102d of main body 102a and detects cover 102b opening and closing.

Puncturing section 52 in which sensor 30 is inserted and locked is provided in the corner of lower edge 102d in main body 102a. Laser puncturing unit 53 (used in Embodiment 1) is incorporated to face puncturing section 52. In addition, sensor cartridge 106 is removably loaded in the vicinity of puncturing section 52 and laser puncturing unit 53. Sensor cartridge 106 is inserted and removed by opening cover 102b at the second open angle. In addition, laser puncturing unit 53 performs puncturing in a state in which cover 102b is open at the first angle (about 30 degrees) as shown in FIG. 20. By performing puncturing at the first open angle, cover 102b blocks laser light 53a, so that laser light 53a does not erroneously leak outside and safety is provided.

Electrical circuit section 55 is provided above laser puncturing unit 53. In addition, battery 108 is removably loaded between electrical circuit section 55 and upper edge 102e of housing 102. Negative pressure means 107 is provided above sensor cartridge 106. Negative pressure means 107 is coupled to puncturing section 52 via negative pressure path 107a.

Now, each part will be explained in detail.

Electrical circuit section 55 is operated by supplying power from battery 108. Electrical circuit section 55 receives signals from sensor 30 and signals from skin detecting sensor 47 as input. Electric circuit section 55 measures the blood sugar level of blood 16 based on the signal from sensor 30 and displays the measurement value on display section 56 (see FIG. 22).

Sensor cartridge 106 is made of resin and has an approximately rectangular solid shape. Case 106k of sensor cartridge 106 contains sensor storing chamber 106a in which sensors 30 are stacked and stored, desiccant storing chamber 106c in which desiccant 106b is stored and conveying means 106d that is provided below desiccant storing chamber 106c and conveys sensor 30.

Conveying means 106d is composed of slide plate 106f and spring 106g that biases slide plate 106f. Slide plate 106f conveys the bottom sensor 30, among sensors 30 stacked and stored in sensor storing chamber 106a, from outlet 106e to puncturing section 52. Slide plate 106f returns to the original position (initial state) by the force of spring 106 after finishing conveying sensor 30. Here, skin detecting sensor 47, which is a skin detecting section, is provided in sensor 30 conveyed by slide plate 106f. Sensor 30 is replaced every time a series of puncturing, measurement and test is performed. Therefore, skin detecting sensor 47 mounted in sensor 30 is replaced at the same time, so that sanitation is provided and ease of maintenance is provided.

Figure 21:
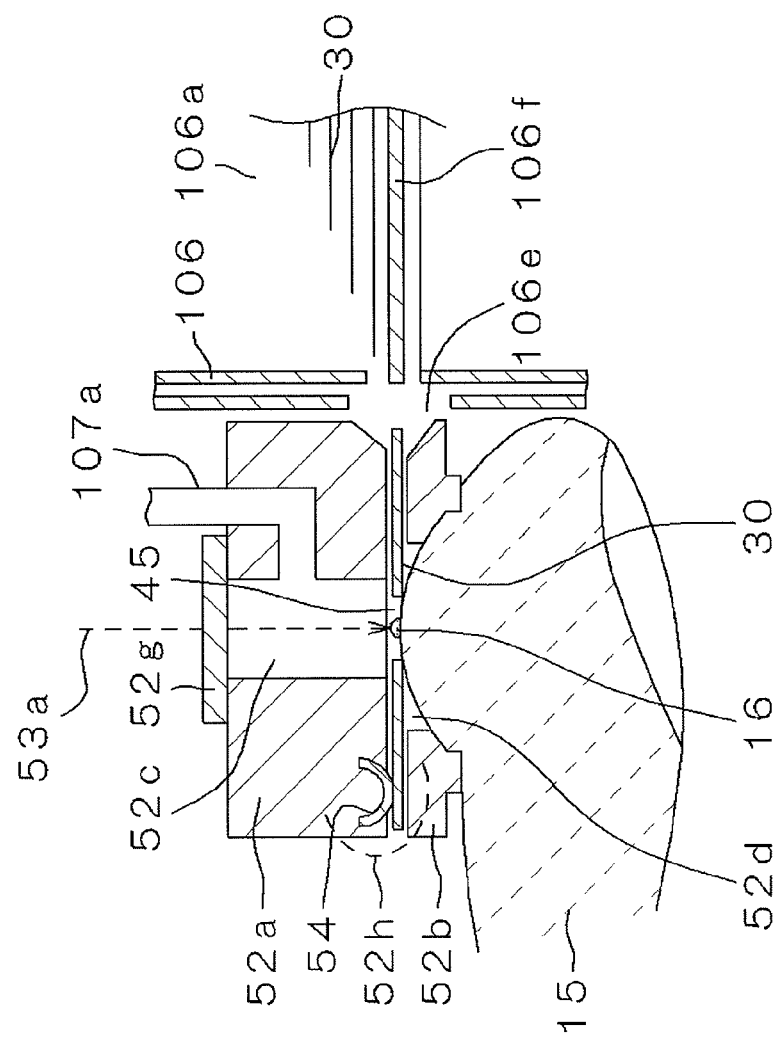
FIG. 21 is a cross sectional view showing a puncturing section and its neighborhood in the blood test apparatus according to Embodiment 6.

FIG. 21 is a cross sectional view showing the above-described puncturing section 52 and its neighborhood.

As shown in FIG. 21, puncturing section 52 is composed of upper holder 52a and lower holder 52b. The bottom sensor 30, among sensors 30 stacked and stored in sensor storing chamber 106a, is conveyed to puncturing section 52 and sandwiched and fixed between upper holder 52a and lower holder 52b.

On side of puncturing section 52 is coupled to outlet 106e of sensor cartridge 106, and connector 54 is mounted in the other side of puncturing section 52 (actually, upper holder 52a constituting puncturing section 52). Connector 54 is provided in the position to contact connection electrodes 32a to 35a corresponding to detection electrodes 32 to 35 of sensor 30 set in puncturing section 52 with connection electrodes 49a and 49b (see FIG. 4 and FIG. 5) corresponding to skin detecting electrodes 47a and 47b constituting a skin detecting section.

Through hole 52c is provided in approximately the center of upper holder 52a. The upper surface of through hole 52c is sealed with transparent film 52g (to allow laser light 53a to pass through). Negative pressure path 107a extending from negative pressure means 107 is coupled to through hole 52c, and therefore, it is possible to apply a negative pressure to the inside of through hole 52c.

Lower holder 52b, which is the other holder constituting puncturing section 52, is biased upward by leaf spring 52h. Through hole 52d is formed in approximately the center of lower holder 52b. Through hole 52d, storing section 45 (see FIG. 4) of sensor 30 and through hole 52c formed in upper holder 52a are formed on a straight line, and laser light 53a passes through their interiors to puncture skin 15. When skin 15 is punctured, blood 16 exudes from skin 15 and is taken into storing section 45 in sensor 30.

Figure 22:
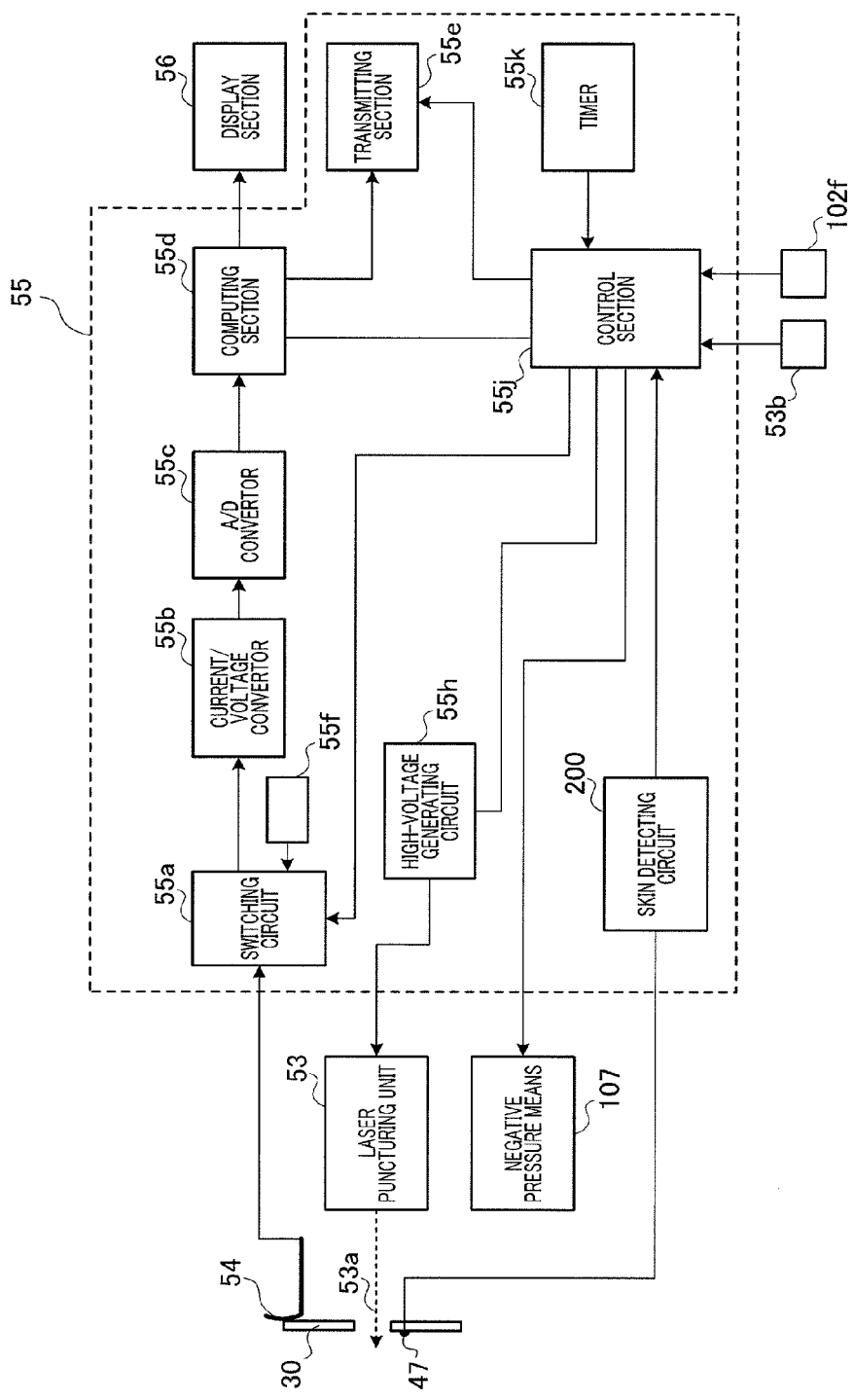
FIG. 22 is a block diagram showing an electrical circuit section and its neighborhood in the blood test apparatus according to Embodiment 6.

FIG. 22 is a block diagram showing the above-described electrical circuit section 55 and its neighborhood.

As shown in FIG. 22, electrical circuit section 55 is configured to include switching circuit 55a, current/voltage convertor 55b, analog/digital convertor (hereinafter "A/D convertor") 55c, computing section 55d, transmitting section 55e, timer 55k, high-voltage generating circuit 55h, skin detecting circuit 200 and control section 55j.

Connection electrodes 32a to 35a (see FIG. 5) in sensor 30 are connected to switching circuit 55a through connector 54 provided in upper holder 52a. Moreover, in the same way, connection electrodes 49a and 49b in sensor 30 corresponding to skin detecting electrodes 47a and 47b (see FIG. 4 and FIG. 5) constituting the skin detecting section provided in sensor 30 are connected to skin detecting circuit 200 through connector 54 provided in upper holder 52a.

Switching circuit 55a receives, at its control terminal, commands from control section 55j, switches between the output voltage from connector 54 to which connection electrodes 49a and 49b that detect the properties of blood are connected and the reference voltage from reference voltage source 55f, and outputs the switched voltage to current/voltage convertor 55b. This reference voltage source 55f may be the ground potential.

Current/voltage convertor 55b is configured by an operational amplifier and so forth, and converts the detected signal outputted from switching circuit 55a to a voltage.

A/D convertor 55c converts the detected signal outputted from current/voltage convertor 55b to a digital signal and outputs the digital signal to computing section 55d.

Computing section 55d performs computation for blood analysis by referring to fixed data and table values stored inside, based on the detected signal converted to a digital signal, according to a command from control section 55j. Computing section 55d outputs the result of measurement and analysis to display section 56 and transmitting section 55e.

Transmitting section 55e has an I/O interface section and outputs the result of measurement and analysis by computing section 55d to the outside according to a command from control section 55j.

Timer 55k measures time for various timings including a puncturing timing, a driving timing of the negative pressure means a skin detection timing and so forth.

High-voltage generating circuit 55h generates a high voltage to drive laser puncturing unit 53 according to a command from control section 55j.

Connection electrodes 49a and 49b corresponding to skin detecting electrodes 47a and 47b are connected to skin detecting circuit 200 through connector 54.

Skin detecting circuit 200 detects contact with skin by measuring electrical conduction or impedance variation in sensor as described later with FIG. 23 to FIG. 26. Skin detecting circuit 200 directly outputs detected signals to control section 55j. Connector 54 to which connection electrodes 49a and 49b corresponding to skin detecting electrodes 47a and 47b are connected and timer 55k are connected through skin detecting circuit 200.

Control section 55j is configured by a microcomputer and so forth, and controls entire blood test apparatus 101. Control section 55j receives, as input, signals from puncturing button 53b that allows laser light 53a to be emitted and open/close sensor 102f that detects cover 102b opening and closing, a skin detected signal from skin detecting circuit 200 and a time measurement signal from timer 55k. Control section 55j measures blood sugar levels and performs blood test (described later with FIG. 27) based on each of the above-described input signals.

Next, operations of skin detecting circuit 200 will be described.

Sensor 30 is characterized by having a skin detecting section composed of skin detecting electrode 47a and skin detecting electrode 47b. After sensor 30 is mounted, skin detecting electrodes 47a and 47b detect contact with skin 15 (see FIG. 4) before puncturing is performed. There are various methods of detecting contact with skin 15 using skin detecting electrodes 47a and 47b. With the present embodiment, a method of measuring electrical conduction (direct current resistance) between skin detecting electrodes 47a and 47b and a method of measuring impedance will be explained.

[Measurement of Direct Current Resistance]

Figure 23:
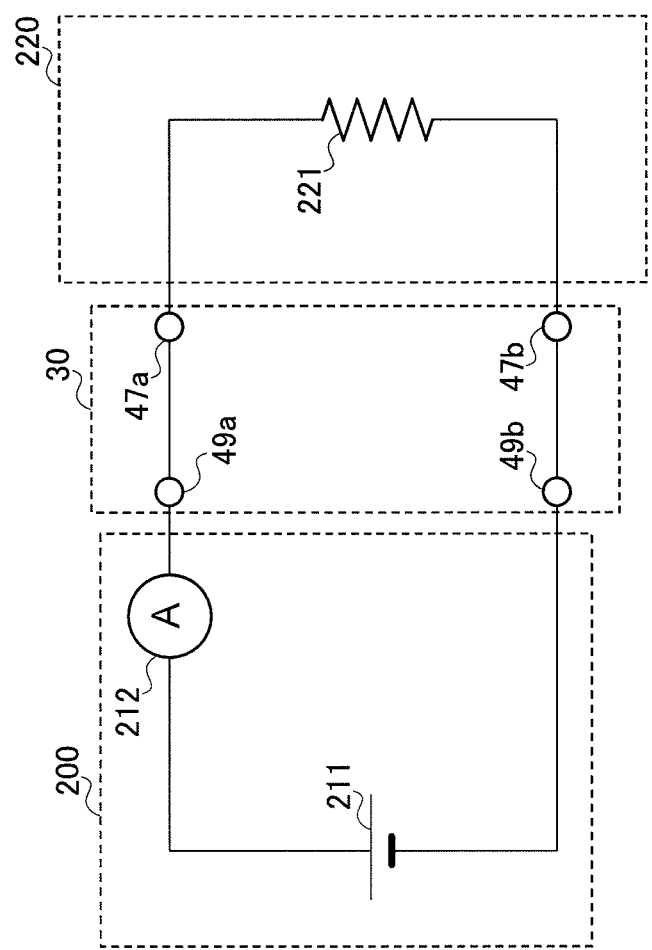
FIG. 23 is a drawing showing a skin detecting circuit, a sensor and a skin-equivalent circuit when a direct current resistance measurement method using the blood test apparatus according to Embodiment 6 is employed.

FIG. 23 is a drawing showing skin detecting circuit 200, sensor 30 and skin-equivalent circuit 220 when the method of measuring direct current resistance is employed.

As shown in FIG. 23, when the method of measuring direct current resistance is employed, skin detecting circuit 200 has direct current power supply 211 and direct current measuring device 212. In addition, skin 15 (see FIG. 4) contacting skin detecting electrodes 47a and 47b constitutes skin-equivalent circuit 220. Skin-equivalent circuit 220 has skin-equivalent resistance 221 between skin detecting electrodes 47a and 47b.

Skin detecting circuit 200 is connected to skin detecting electrodes 47a and 47b through connection electrodes 49a and 49b in sensor 30. To be more specific, the positive side of direct current power supply 211 in skin detecting circuit 200 is connected to skin detecting electrode 47a through direct current measuring device 212 and connection electrode 49a in sensor 30, and the negative side of direct current power supply 211 is connected to skin detecting electrode 47b through connection electrode 49b in sensor 30. When skin 15 (see FIG. 4) contacts between skin detecting electrodes 47a and 47b, skin-equivalent resistance 221 occurs and skin-equivalent circuit 220 is formed.

If the voltage of direct current power supply 211 is fixed in skin-equivalent circuit 220, the current of direct current measuring device 212 and the resistance value of skin-equivalent resistance 220 are inversely related to one another according to the Ohm's law. Therefore, it is possible to detect variations in the resistance value of skin-equivalent resistance 221 due to contact with skin as variation in the current of direct current measuring device 212.

Data of an experiment is as follows.

FIG. 24 is a drawing showing a table of the result of an experiment.

In the skin-equivalent circuit in FIG. 23, the following voltages are applied to connection electrodes 49a and 49b in sensor 30 connected to skin detecting electrodes 47a and 47b in sensor 30 and then current intensities are measured. Voltages are applied between connection electrodes 49a and 49b, and current values are measured in a case in which skin detecting electrodes 47a and 47b do not contact skin (when not contacting skin) and in a case in which skin detecting electrodes 47a and 47b contact skin (when contacting skin).

The result of the experiment obtained by measurement with changed voltages are shown in the table in FIG. 24.

As shown in FIG. 24, since the resistance between connection electrodes 49a and 49b in sensor 30 is reduced due to contact with skin, the current increases. Variations in current intensities are enough to be detected and used in skin detection.

Detection of contact with skin by the method of measuring direct current resistance provides an advantage of enabling a simple configuration and low cost.

[Impedance Measurement]

Figure 25:
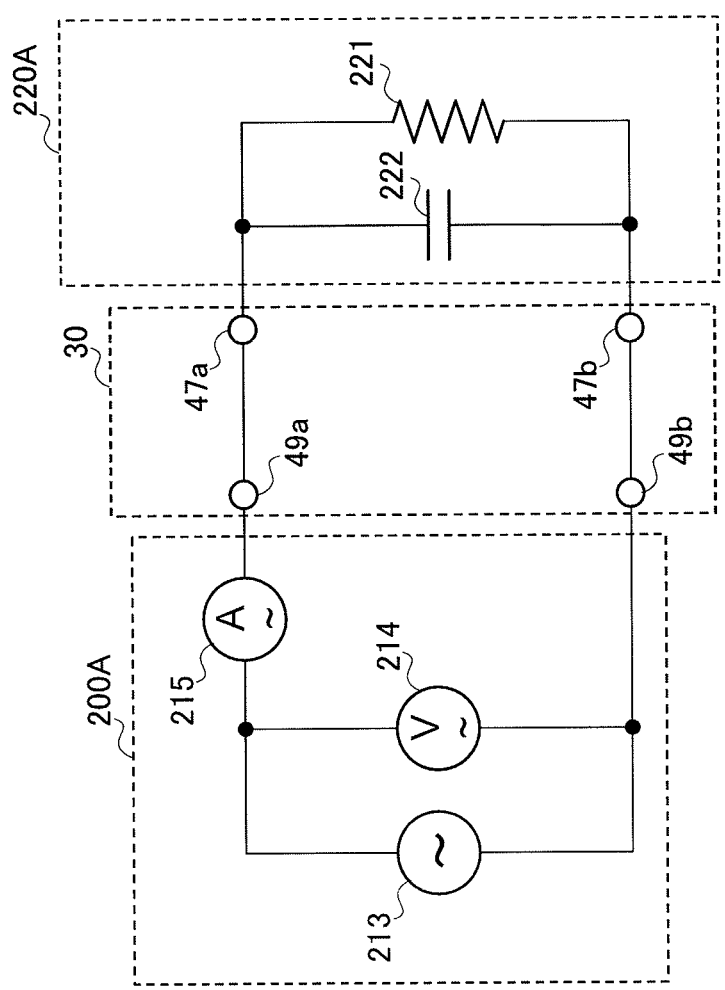
FIG. 25 is a drawing showing a skin detecting circuit, a sensor and a skin-equivalent circuit when an impedance measurement method using the blood test apparatus according to Embodiment 6 is employed.

FIG. 25 is a drawing showing skin detecting circuit 200A, sensor 30 and skin-equivalent circuit 220A when the impedance measurement method is employed.

As shown in FIG. 25, when the impedance measurement method is employed, skin detecting circuit 200A has alternating current power supply 213, alternating voltage measuring device 214 and alternating current measuring device 215 to configure an impedance measurement circuit.

In addition, skin 15 (see FIG. 4) contacting skin detecting electrodes 47a and 47b constitutes skin-equivalent circuit 220A. Skin-equivalent circuit 220A has skin-equivalent resistance 221 and capacitor 222 in parallel between skin detecting electrodes 47a and 47b, and skin-equivalent resistance 221 and capacitor 222 constitute an RC parallel circuit. Here, although skin detecting circuit 200 in FIG. 23 is representatively shown in FIG. 22, skin detecting circuit 200A in FIG. 25 is naturally applicable.

Skin detecting circuit 200A is connected to skin detecting electrodes 47a and 47b through connection electrodes 49a and 49b in sensor 30.

Skin-equivalent circuit 220A has the relationship represented by following equation 1.

(Equation 1)

$$\dot{I} = \dot{V}\left(\frac{1}{R} + j\omega fC\right) \quad [1]$$

$$\therefore R = \left|\frac{\dot{V}}{\dot{I}}\right|\frac{1}{\cos\theta}, \quad C = \left|\frac{\dot{I}}{\dot{V}}\right|\sin\theta.$$

Here, V represents the alternating voltage in complex notation, I represents the alternating current in complex notation, j represents the imaginary unit, ω represents the angular frequency of alternating current power supply 213 and θ represents the phase delay of I from V.

It is possible to calculate resistance value R of skin-equivalent resistance 221 and capacitance Cp of capacitor 222 by applying values measured by alternating voltage measuring device 214 and alternating current measuring device 215 to above-described equation 1.

Data of an experiment is as follows.

FIG. 26 is a drawing showing a table of the result of an experiment.

In the skin-equivalent circuit shown in FIG. 25, an alternating power supply is applied to connection electrodes 49a and 49b in sensor 30 connected to skin detecting electrodes 47a and 47b in sensor 30, and capacitance Cp and resistance Rp between one end of connection electrode 49a and one end of connection electrode 49b connected to skin detecting electrodes 47a and 47b. A predetermined signal (20 MHz) is applied to connection electrodes 49 and 49b, and then capacitance Cp and resistance Rp between connection electrodes 49a and 49b are measured. This case is equivalent to a parallel connection of a capacitor and a resistor between connection electrodes 49a and 49b.

The result of the experiment of a plurality of measurements are shown in the table in FIG. 26.

As shown in FIG. 26, capacitance Cp is increased and resistance Rp is reduced due to contact with skin. Both variations are enough to be detected and allowed to be used for skin detection.

As described above, as for the detection of contact with skin using the impedance measurement method, capacitance Cp increases when skin 15 (see FIG. 4) contacts skin detecting electrodes 47a and 47b, and even if skin 15 does not contact detecting electrodes 47a and 47b but merely comes close to skin detecting electrodes 47a and 47b, capacitance Cp increases. Therefore, it is possible to detect skin 15 coming close to lower holder 52b even if skin 15 has not yet contacted skin detecting electrodes 47a and 47b. For example, a negative pressure is supplied by negative pressure means 107 (see FIG. 22) before puncturing. It is possible to use negative pressure means 107 (see FIG. 22) as a criterion to start puncturing.

Skin detecting operations of skin detection circuits 200 and 200A have been described.

Next, operations of blood sugar level measurement will be explained.

After skin detecting sensor 47, which is a skin detecting section, composed of skin detecting electrodes 47a and 47b, detects skin 15, puncturing button 53b is pressed and laser puncturing unit 53 punctures skin 15. Then, the properties of blood 16 exuding by puncturing are measured. In a measurement operation to measure the properties of blood 16, switching circuit 55a is switched and detection electrode 32 (see FIG. 5) is connected to current/voltage convertor 55b. In addition, detection electrode 33, which is a detecting electrode to detect blood 16 flowing in, is connected to reference voltage source 55f. Then, a certain voltage is applied between detection electrode 32 and detection electrode 33. In this state, when blood 16 flows in, a current flows between detection electrodes 32 and 33. This current is converted to a voltage by current/voltage convertor 55b and its voltage value is converted to a digital value by A/D convertor 55c. Then, the digital value is outputted to computing section 55d. Computing section 55d detects that blood 16 has sufficiently flowed in based on that digital value. Here, at this time, the operation of negative pressure means 107 is turned off.

Next, glucose, a blood component, will be measured. To measure the glucose level, first, switching circuit 55a is switched by a command from control section 55j, and detection electrode 32 serving as a working electrode for measuring the glucose level is connected to current/voltage convertor 55b. In addition, detection electrode 34 serving as a counter electrode for measuring the glucose level is connected to reference voltage source 55f.

Here, for example, while the glucose in blood and its oxidation-reduction enzyme react for a given period of time, current/voltage convertor 55b and reference voltage source 55f are turned off. Then, after a certain period of time (1 to 10 seconds) has passed, a certain voltage (0.2 to 0.5 V) is applied between detection electrodes 32 and 34 by a command from control section 55j. By this means, a current flows between detection electrodes 32 and 34. This current is converted into a voltage by current/voltage convertor 55b, and its voltage value is converted into a digital value by A/D convertor 55c. Then, this digital value is outputted to computing section 55d. Computing section 55d calculates the glucose level based on this digital value.

After the glucose level is measured, the Hct value is measured. The Hct value is measured as follows. First, switching circuit 55a is switched by a command from control section 55j. Then, detection electrode 35 serving as a working electrode for measuring the Hct value is connected to current/voltage convertor 55b. In addition, detection electrode 32 serving as a counter electrode for measuring the Hct value is connected to reference voltage source 55f.

Next, a certain voltage (2 V to 3 V) is applied between detection electrodes 35 and 32 from current/voltage convertor 55b and reference voltage source 55f by a command from control section 55j. The current flowing between detection electrodes 35 and 32 is converted into a voltage by current/voltage convertor 55b, and its voltage value is converted into a digital value by A/D convertor 55c. Then, this digital value is outputted to computing section 55d. Computing section 55d calculates the Hct value based on this digital value.

With reference to a calibration curve or calibration curve table determined in advance, the glucose level is corrected with the Hct value using the Hct value and the glucose level resulting from this measurement. The corrected result is displayed on display section 56. In addition, the correction result is transmitted from transmitting section 55e to an injection device to inject insulin.

Although measurement of blood sugar levels has been explained as an example, the present invention is applicable to measurement of levels of blood components such as lactic acid and cholesterol other than blood sugar by changing reagent 50 in sensor 30.

Next, a test method using blood test apparatus 101 will be explained.

Figure 27:
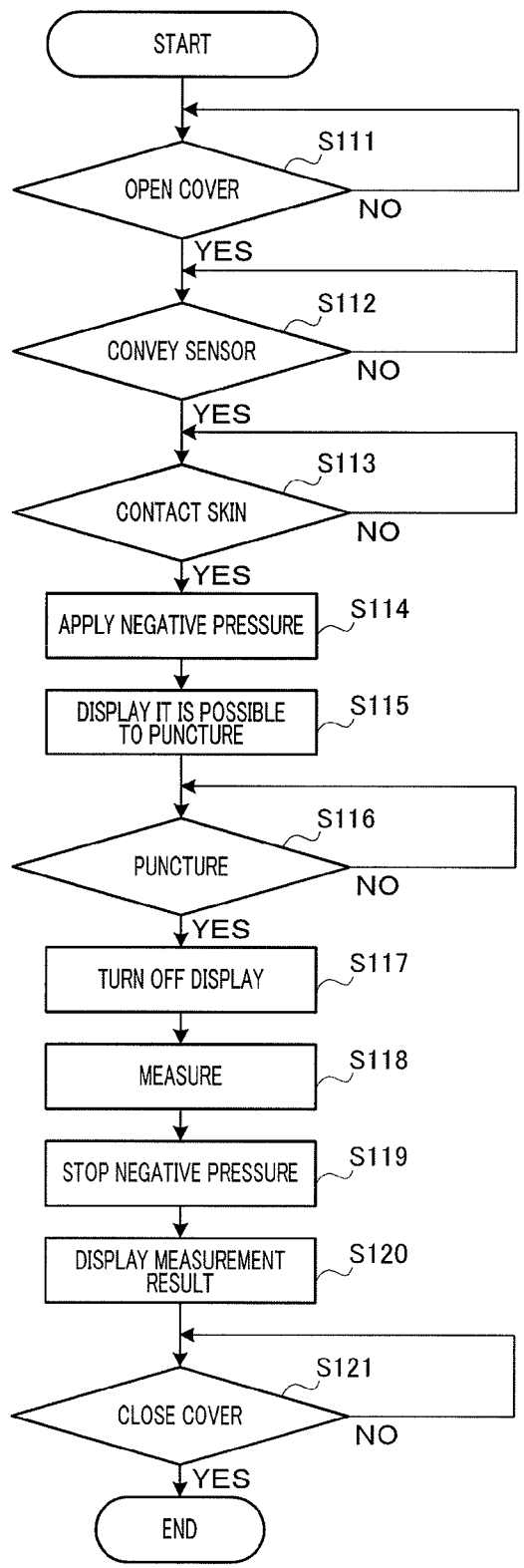
FIG. 27 is a flowchart of a blood test method using the blood test apparatus according to Embodiment 6.

FIG. 27 is a flowchart of a blood test method using blood test apparatus 101. S represents each step in the figure.

First, in step S111, open/close detecting sensor 102f detects cover 102b (see FIG. 20) in blood test apparatus 101 opening.

In step S112, conveying means 106d (see FIG. 20) moves slide plate 106f toward outlet 106e of sensor cartridge 106. As a result of this, it is possible to convey the bottom sensor 30 among stacked and stored sensors 30 to puncturing section 52. By this means, sensor 30 in which skin detecting sensor 47 is mounted is conveyed to puncturing section 52 every time a series of puncturing, measurement and test is performed. After the conveyance is finished, slide plate 106f is returned to a standby state by the force of spring 106g.

In step S113, control section 55j detects whether blood test apparatus 101 contact skin 15 of the patient based on the detected signals from skin detection circuits 200 and 200A. Contact with skin 15 is detected by measuring the resistance value between connection electrodes 49a and 49b respectively connecting skin detecting electrodes 47a and 47b constituting the skin detecting section provided in sensor 30 (see FIG. 23 and FIG. 24), or by measuring impedance (see FIGS. 25 and 26).

When the contact with skin 15 is detected, control section 55j operates negative pressure means 107 to apply a negative pressure to puncturing section 52 in step 114. A negative pressure is applied to skin 15 through negative pressure path 107a, through hole 52c, storing section 45 and through hole 52d as shown in FIG. 21. Skin 15 swells by applying a negative pressure.

When the current varies by the operation of negative pressure means 107, or when timer 55k measures a predetermined period of time, it is determined that skin 15 in lower holder 52b sufficiently has swelled by a negative pressure, and the step moves to step S115.

In step S115, control section 55j displays on display section 56 that it is possible to perform puncturing on the condition that skin detecting sensor 47, which is a skin detecting section, composed of skin detecting electrodes 47a and 47b detects contact with skin 15.

In step S116, control section 55j waits until puncturing button 53b is pressed.

When puncturing button 53b is pressed, in step S117, control section 55j turns off the indication on display section 56 in step S115.

In step S118, control section 55j measures the blood sugar level of blood 16. That is, blood 16 exuding by puncturing skin 15 is taken into storing section 45 in sensor 30. This blood 16 taken into storing section 45 is introduced into detecting section 46 at a breath (at a fixed flow rate) by capillary action of supply path 44. Control section 55j measures the blood sugar level of blood 16.

In step S119, control section 55j turns off negative pressure means 107.

In step S120, control section 55j displays the measured blood sugar level on display section 56. Here, negative pressure means 107 may be turned off at the time blood 16 reaches detection electrode 33.

In step S121, open/close detecting sensor 102f detects cover 102b (see FIG. 20) of blood test apparatus 101 being closed and the flow ends based on the detection result.

In the above-described step S112, a new sensor 30 is conveyed every time puncturing is performed, so that skin detecting electrodes 47a and 47b constituting skin detecting sensor 47 provided in sensor 30 are also replaced every time puncturing is performed. Since skin detecting sensor 47 that detects skin 15 is replaced every time a series of puncturing, measurement and test is performed, sanitation is provided. In addition, there is no trouble of regular maintenance of the skin detecting sensor.

Moreover, resistance values outputted from skin detecting electrodes 47a and 47b are used as a criterion to start negative pressure means 107 in step S114, so that it is possible to detect the start without wasting power. Moreover, since the logical product of signals outputted from skin detecting electrodes 47a and 47b is used as a criterion for puncturing in step S116, laser light 53a is not emitted erroneously outward, and therefore, safety is provided.

The above description is illustration of preferred embodiments of the present invention and the scope of the invention is not limited to this.

Although the names "blood sensor" and "blood test apparatus" are used in the apparatus of the invention for convenience of explanation, "biosensor", "blood analysis apparatus", "puncturing apparatus" and so forth are possible. Moreover, although the name "blood analysis method" is used in the method of the invention, "blood test method" and so forth are possible. Generally, the names vary depending on the types of blood samples.

In addition, the number, the arrangement (position, interval and so forth) and the shape (circle, arc, concentric circle and so forth) of each of parts constituting a sensor, such as skin detecting electrodes, are not limited, and the shape (with or without a hole), the structure (stacking order of each sensor component) and the electrode structure (through-hole interconnection and so forth) of a sensor are also not limited.

In the same way, the type, the number, the connection method and so forth of each of parts constituting the above-described blood test apparatus, such as a laser puncturing means, are not limited.

The disclosure of Japanese Patent Application No. 2008-027462, filed on Feb. 7, 2008, including the specification, drawings and abstract, is incorporated herein by reference in its entirety.

INDUSTRIAL APPLICABILITY

The blood sensor, the blood test apparatus and the blood analysis method according to the present invention are applicable to a blood analysis apparatus that samples blood from skin by a blood sampling means and analyzes components of blood. By using the blood sensor according to the present invention, it is possible to make good use of exuding blood and provide sanitation by replacing sensors, so that the blood sensor is applicable to a blood test apparatus and so forth.

The invention claimed is:

1. A blood sensor that analyzes a component in a blood sample, the blood sensor comprising:
   a skin detecting section comprising a skin detection electrode arranged on a surface of a blood sensor for analyzing a component in a blood sample, the skin detection electrode being arranged to directly contact skin from which the blood sample is exuded; and
   a connection electrode that connects with the skin detection electrode comprised in the skin detecting section and outputs a detection result by the skin detecting section to outside the blood sensor,
   wherein the blood sensor has a planar plate like shape and a hole therein leading to a blood storing section in the blood sensor in which the blood sample is to be stored, and the blood sensor is configured to be attached to a blood sensor apparatus comprising an electrical circuit section, and is further configured to be attached so as to contact the connection electrode with the electrical circuit section.

2. The blood sensor according to claim 1, wherein the skin detecting section has one or more skin detecting electrodes.

3. The blood sensor according to claim 1, wherein the skin detecting section is mounted in a blood supply side.

4. The blood sensor according to claim 1, wherein the skin detecting section is arranged so as not to contact at least one of an oxidation-reduction enzyme and an electron mediator.

5. The blood sensor according to claim 1, wherein the skin detecting section is arranged not to contact a reactive reagent that causes an oxidation-reduction reaction.

6. The blood sensor according to claim 1, wherein the skin detecting section is arranged not to contact a reagent.

7. The blood sensor according to claim 1, further comprising:
   a blood component measuring section that measures an item related to a concentration of a substance to be analyzed in the blood sample.

8. The blood sensor according to claim 7, wherein:
   the blood component measuring section is an analysis electrode that measures a blood component and is composed of a working electrode and a counter electrode; and
   the skin detecting section is provided as a separate part from the analysis electrode.

9. The blood sensor according to claim 1, further comprising:
   a plate-like base body;
   a blood storing section provided in an end part or approximately a center part of the base body;
   a supply path having one side coupled to the storing section and the other side coupled to an air hole; and
   a detection electrode that is provided on one surface of the supply path and that is configured to detect a blood which has flowed into the supply path.

10. The blood sensor according to claim 9, wherein skin detecting sections are arranged in two spots sandwiching the storing section to face one another.

11. The blood sensor according to claim 9, wherein skin detecting sections are arranged in four spots sandwiching the storing section to face each other.

12. The blood sensor according to claim 9, wherein the detecting section comprises two arc members disposed so that interiors of the two arc members face each other across the storing section.

13. The blood sensor according to claim 9, wherein skin detecting sections are concentrically arranged around a center of the storing section.

14. A blood test apparatus in which a blood sensor according to claim 1 is mounted, comprising:
   a skin detecting circuit that detects contact or approach to skin based on a signal from the connection electrode.

15. The blood test apparatus according to claim 14, wherein the skin detecting circuit measures an impedance of skin and detects contact or approach to the skin.

16. The blood test apparatus according to claim 14, wherein the skin detecting circuit measures variation in a capacitance of skin and detects contact or approach to the skin.

17. A blood sensor that analyzes a component in a blood sample, the blood sensor comprising:
a plate-like base body;
a blood storing section provided in an end part or approximately a center part of the base body;
a supply path having one side coupled to the storing section and the other side coupled to an air hole; and
a detection electrode that is provided on one surface of the supply path and detects a property of blood,
a skin detecting section that is arranged to contact skin from which the blood sample is exuded; and
a connection electrode that outputs a detection result by the skin detecting section to outside the blood sensor;
wherein the base body includes: a substrate having a rear surface on which the detection electrode is provided; a spacer that is mounted on a rear surface side of the substrate and has a slit to constitute part of the supply path; and a cover mounted on a rear surface side of the spacer;
wherein the storing section is formed by a substrate hole provided in the substrate, a spacer hole that is coupled to the substrate hole and provided in the spacer and a cover hole provided in the cover; and
wherein the skin detecting section is arranged in the storing section, and the skin detecting section is arranged on a lower surface side of the substrate in the storing section.

18. A blood sensor that analyzes a component in a blood sample, the blood sensor comprising:
a plate-like base body;
a blood storing section provided in an end part or approximately a center part of the base body;
a supply path having one side coupled to the storing section and the other side coupled to an air hole;
a detection electrode that is provided on one surface of the supply path and detects a property of blood;
a skin detecting section that is arranged to contact skin from which the blood sample is exuded; and
a connection electrode that outputs a detection result by the skin detecting section to outside the blood sensor,
wherein the base body includes: a substrate having a surface on which the detection electrode is provided; a spacer that is mounted on a surface side of the substrate and has a slit to constitute part of the supply path; and a cover mounted on a surface side of the spacer, and
wherein the skin detecting section is arranged in the storing section on a rear surface of the substrate.

* * * * *